US008900603B2

(12) United States Patent
Esfand et al.

(10) Patent No.: US 8,900,603 B2
(45) Date of Patent: Dec. 2, 2014

(54) LOCAL DELIVERY OF DRUGS FROM SELF ASSEMBLED COATINGS

(75) Inventors: Roseita Esfand, Mississauga (CA); J. Paul Santerre, Whitby (CA); Sylvia Tjahyadi, Toronto (CA); Bernadette Ilagan, Toronto (CA)

(73) Assignee: Interface Biologics, Inc., Toronto (CA)

( * ) Notice: Subject to any disclaimer, the term of this patent is extended or adjusted under 35 U.S.C. 154(b) by 0 days.

(21) Appl. No.: 13/516,913

(22) PCT Filed: Dec. 20, 2010

(86) PCT No.: PCT/CA2010/002036
§ 371 (c)(1),
(2), (4) Date: Feb. 20, 2013

(87) PCT Pub. No.: WO2011/072398
PCT Pub. Date: Jun. 23, 2011

(65) Prior Publication Data
US 2013/0142834 A1    Jun. 6, 2013

Related U.S. Application Data

(60) Provisional application No. 61/287,862, filed on Dec. 18, 2009.

(51) Int. Cl.
*A61K 47/34* (2006.01)
*A61K 31/337* (2006.01)
*A61K 31/436* (2006.01)
*A61L 29/08* (2006.01)
*A61L 29/16* (2006.01)
*A61L 31/10* (2006.01)
*A61L 31/16* (2006.01)
*C08G 65/00* (2006.01)
*C08L 71/02* (2006.01)

(52) U.S. Cl.
CPC .............. *A61K 47/34* (2013.01); *A61K 31/337* (2013.01); *A61K 31/436* (2013.01); *A61L 29/085* (2013.01); *A61L 29/16* (2013.01); *A61L 31/10* (2013.01); *A61L 31/16* (2013.01); *C08G 65/007* (2013.01); *C08L 71/02* (2013.01); *A61L 2300/416* (2013.01); *C08L 2203/02* (2013.01)
USPC ............ 424/400; 560/158; 514/785; 514/449

(58) Field of Classification Search
USPC ................... 424/400; 560/158; 514/785, 449
See application file for complete search history.

(56) References Cited

U.S. PATENT DOCUMENTS

| | | | |
|---|---|---|---|
| 3,929,922 | A | 12/1975 | Wilke et al. |
| 5,362,718 | A | 11/1994 | Skotnicki et al. |
| 5,665,772 | A | 9/1997 | Cottens et al. |
| 6,127,507 | A | 10/2000 | Santerre |
| 6,770,725 | B2 | 8/2004 | Santerre |
| 2003/0097120 | A1 | 5/2003 | Santerre |
| 2003/0204238 | A1 | 10/2003 | Tedeschi |
| 2005/0131527 | A1 | 6/2005 | Pathak |
| 2007/0037891 | A1 | 2/2007 | Esfand et al. |
| 2007/0190103 | A1 | 8/2007 | Hossainy et al. |
| 2011/0104228 | A1 | 5/2011 | Esfand et al. |

FOREIGN PATENT DOCUMENTS

| | | |
|---|---|---|
| CA | 2470524 A1 | 7/2003 |
| CA | 2484269 A1 | 11/2003 |
| CA | 2555364 A1 | 9/2005 |
| CN | 101203250 A | 6/2008 |
| WO | WO-02/098477 A2 | 12/2002 |
| WO | WO-2007/004067 A2 | 1/2007 |
| WO | WO-2007/040557 A1 | 4/2007 |
| WO | WO 2007/148230 * | 12/2007 |
| WO | WO-2007/148230 A2 | 12/2007 |
| WO | WO-2008/076345 A1 | 6/2008 |
| WO | WO-2009/043174 A1 | 4/2009 |
| WO | WO-2009/049426 A1 | 4/2009 |
| WO | WO 2009049426 A1 * | 4/2009 |
| WO | WO-2010/025398 A1 | 3/2010 |

OTHER PUBLICATIONS

Benneche et al., "Pyrimidinones as reversible metaphase arresting agents," Eur J Med Chem. 28:463-72 (1993).
Gurd, "Carboxymethylation," Methods Enzymol. 11:532-41 (1967).
Herriott, "Reactions of Native Proteins with Chemical Reagents," Adv Protein Chem. 3:169-225 (1947).
Herzig et al., "Bifunctional reagents and protein structure determination. The reaction of phenolic disulfonyl chlorides with lysozyme," Biopolymers. 2:349-60 (1964).
Hunter et al., "The Reaction of Imidoesters with Proteins and Related Small Molecules," J Am Chem Soc. 84(18):3491-3504 (1962).
McAlpine et al., "Revised NMR assignments for rapamycin," J Antibiodics. 44(6):688-90 (1991).
McKenzie et al., "Development of a bifunctional crosslinking agent with potential for the preparation of immunotoxins," J Protein Chem. 7(5):581-92 (1988).
Peppas et al., "New challenges in biomaterials," Science. 263(5154):1715-20 (1994).
Pehn, "Choosing a drug-eluting stent: A comparison between CYPHER and TAXUS," Rev Cardiovasc Med. 6( suppl 1):S13-S21 (2005).

(Continued)

*Primary Examiner* — Anoop Singh
*Assistant Examiner* — Anna Falkowitz
(74) *Attorney, Agent, or Firm* — Clark & Elbing LLP; Kristina Bieker-Brady

(57) ABSTRACT

The invention relates to oligofluorinated coatings and their use in drag delivery The oligofluorinated coatings are compositions comprising formula (XVII). These coatings are used in a method of delivering a biologically active agent to a tissue surface in a mammalian tissue This method occurs by contacting the surface with the coating including an oligofluorinated oligomer and a biologically active agent wherein the coating resides on the tissue surface and release the biologically active agent to the tissue surface.

10 Claims, 3 Drawing Sheets

(56) References Cited

OTHER PUBLICATIONS

Smyth et al., "Some Reactions of N-Ethylmaleimide," J Am Chem Soc. 82(17):4600-04 (1960).
Smyth et al., "Reactions of N-Ethylmaleimide with peptides and amino acids," Biochem J. 91:589-95 (1964).
Tietze et al., "Squaric acid diethyl ester: A new coupling reagent for the formation of drug biopolymer conjugates. Synthesis of squaric acid ester amides and diamides," Chem Ber. 124:1215-21 (1991).
Van Duyne et al., "Atomic structure of the rapamycin human immunophilin FKBP-12 complex," J Am Chem Soc. 113(13):7433-34 (1991).
Webb et al., "Synthesis of 1-(aminooxy)-4-[(3-nitro-2-pyridyl)dithio]butane and 1-(aminooxy)-4-[(3-nitro-2-pyridyl)dithio]but-2-ene, novel heterobifunctional cross-linking reagents," Bioconjugate Chem. 1:96-9 (1990).
Wetz et al., "Synthesis of 'long,' hydrophilic, protein-cross-linking reagents," Anal Biochem. 58(2):347-60 (1974).
Wong et al., "Uridine diphosphate galactose 4-epimerase. Alkylation of enzyme-bound diphosphopyridine nucleotide by p-(bromoacetamido)phenyl uridyl pyrophosphate, an active-site-directed site-directed irreversible inhibitor," Biochem. 18(24):5337-41 (1979).
Office Action for Chinese Appliication No. 201080064081.1, dated Apr. 30, 2014 (16 pages).
International Preliminary Report on Patentability for International Application No. PCT/CA2010/002036, mailed Jun. 28, 2012 (8 pages).

\* cited by examiner

Assessment of anti-fouling properties of balloon coating

Nylon + BSA             Compound 1 + BSA

LOCAL DELIVERY OF DRUGS FROM SELF ASSEMBLED COATINGS

CROSS-REFERENCE TO RELATED APPLICATIONS

This application is the U.S. National Stage of International Application No. PCT/CA2010/002036, filed Dec. 20, 2010, which claims benefit of U.S. Provisional Application No. 61/287,862, filed Dec. 18, 2009, each of which is hereby incorporated by reference.

BACKGROUND OF THE INVENTION

The invention relates to the coalescence of fluorinated oligomers and therapeutic agents as self assembled coatings and formulations, and their use in drug delivery.

Localized therapeutic delivery, including therapies that control the proliferation or growth of tissue into the open path of blood vessels, has been achieved with implantable devices such as drug eluting stents (DES). However, these devices are imperfect and can result in frequent side effects. The presence of residual foreign material can elicit a damaging inflammatory response and induce coagulation. Various techniques can be employed to modify the surface of implantable devices to improve biocompatibility and thromboresistance as well as impart properties different from those of the device material, e.g., infection resistance (i.e., via the delivery of a biologically active agent), radiopacity, conductivity, etc. In the DES arena, these techniques have had limited success.

Transient medical devices, i.e., devices that reside in the body for very short periods of time (inserted and removed) can also be used as localized therapeutic delivery vehicles. The use of a transient medical device (e.g., balloon catheter, guidewire, syringe needle, or probes) would be more advantageous over permanent, implantable medical devices as there are no long term biocompatibility issues.

As a result of the issues associated with DES, the concept of using a drug eluting balloon (DEB) catheter to locally deliver an anti-restenotic drug, such as paclitaxel, at the site of arterial disease is now seen as an opportunity to provide an alternative treatment which circumvents many of the concerns associated with DES. The DEB catheter would deliver a therapeutic amount of drug effectively upon inflation while in contact with the lumen wall for a limited time.

The DEB catheter approach has been the subject of several clinical trials since 2006. However, the outcome of many of these trials, including several repeated by the same companies with slightly reformulated materials, has been one of limited successes, due to inherent limitations in the carrier molecules for the drugs. The general strategy has been to coat the balloon catheter with established dye agents or pharmaceutical emulsifying materials that have an established regulatory history (see U.S. Patent Publication No. 20060020243). The result is a less than optimal performance in terms of retention onto the balloon during intra-luminal delivery (e.g., 90% of drug can be lost even before reaching the targeted tissues, with some absorbed into the balloons, and <6% being transferred to the diseased tissue) (see Axel De Labriolle et al., Catheterization and Cardiovascular Interventions 73:643 (2009)).

These results demonstrate a need for a synthetic modular approach to address the limitations of drug retention with efficient and preferential transfer of drug into the local tissues. To address these imitations, the carrier molecule needs to be designed with low blood activation with reduced local delivery of the carrier system upon arrival of the balloon at the target site.

SUMMARY OF THE INVENTION

The methods and compositions of the invention feature branched oligomeric compounds (e.g., oligofluorinated coatings and formulations), and their use in drug delivery.

In a first aspect, the invention features a composition of formula

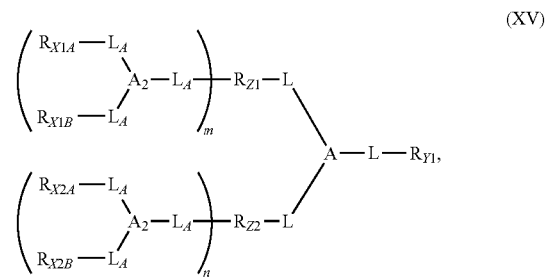

(XV)

where
m and n are both 0, or m and n are both 1;
each A and $A_2$ is a trifunctional monomer having a molecular weight between 50-3500 Da;
each L and $L_A$ is, independently, a linker;
each $R_{X1A}$, $R_{X1B}$, $R_{X2A}$, and $R_{X2B}$ is, independently, a water insoluble segment having a molecular weight between 200-3,500 Da; and
$R_{Y1}$ is a non-halogenated organic segment having a molecular weight between 200-3,500 Da; and
when m and n are both 1, each of $R_{Z1}$ and $R_{Z2}$ is, independently, a difunctional water insoluble segment having a molecular weight between 50-3,500 Da, or
when m and n are both 0, each of $R_{Z1}$ and $R_{Z2}$ is, independently a water insoluble segment having a molecular weight between 200-3,500 Da.

In some embodiments, the composition has the following formula

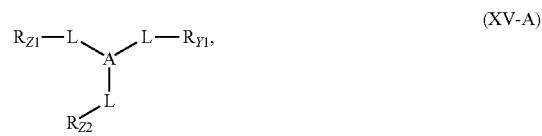

(XV-A)

where
A is a trifunctional monomer having a molecular weight between 50-3500 Da; each L is, independently, a linker;
$R_{Z1}$ and $R_{Z2}$ are each, independently, a water insoluble segment (e.g., an organohalide segment) having a molecular weight between 200-3,500 Da; and
$R_{Y1}$ is a non-halogenated organic segment having a molecular weight between 100-3,500 Da.

In some embodiments, A is a trifunctional monomer having a molecular weight between 50-1000 Da; each L is, independently, a linker; $R_{Z1}$ and $R_{Z2}$ are each, independently, water insoluble segments such as an organohalide segment having a molecular weight between 200-3,500 Da; and $R_{Y1}$ is a non-halogenated organic segment having a molecular weight between 100-3,500 Da.

In other embodiments, the composition is described by the following formula (XV-B):

In other embodiments, the composition has the following formula

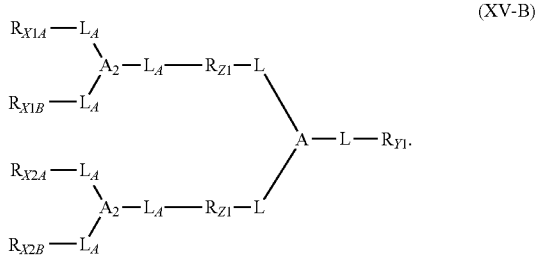

(XV-B)

where each A and $A_2$ is a trifunctional monomer having a molecular weight between 50-3500 Da; each L and $L_A$ is, independently, a linker; each $R_{X1A}$, $R_{X1B}$, $R_{X2A}$, and $R_{X2B}$ are each, independently, a water insoluble segment having a molecular weight between 200-3,500 Da; and $R_{Y1}$ is a non-halogenated organic segment having a molecular weight between 100-3,500 Da, and each $R_{Z1}$ is, independently, a difunctional water insoluble segment having a molecular weight between 100-3,500 Da. In some embodiments, $R_{Z1}$ is a fluorinated diol. It would be understood by those skilled in the art that the R-like branches could be increased to further generations of the branching. Likewise it would be understood by those skilled in the art that the $R_{Y1}$ moiety could also have branching segments if desired. In some embodiments, A includes a triol.

In other embodiments, A includes a glycerol, trimethylolpropane (TMP), trimethylolethane (TME), trimesic acid (TMA), or tris(hydroxyethyl)isocyanurate (THEIC).

In any of the above formulas, $R_{Y1}$ may be branched or unbranched.

In certain embodiments, $R_{Y1}$ is a linear or branched polyethylene glycol, zwitterions (including zwitterionic surfactant moieties, e.g., alkyl betaines, such as alkyl amidopropyl betaine, sulfobetaines and alkyl sultaines, alkyl ether hydroxylpropyl sultaines, and alkylamidopropylhydroxy sultaines), or polyvinylpyrrolidone.

In other embodiments, $R_{Z1}$ and $R_{Z2}$ are each, independently, a polyfluoroorgano, a polysiloxane, or polyolefin group, or wherein each of $R_{X1A}$, $R_{X1B}$, $R_{X2A}$, $R_{X2B}$ are each, independently, a polyfluoroorgano, a polysiloxane, or polyolefin group.

In still other embodiments, $R_{Z1}$ and $R_{Z2}$ are each, independently, a silicone group, or wherein each of $R_{X1A}$, $R_{X1B}$, $R_{X2A}$, $R_{X2B}$ are each, independently, a silicone group.

In other embodiments, the composition is described by the following formula,

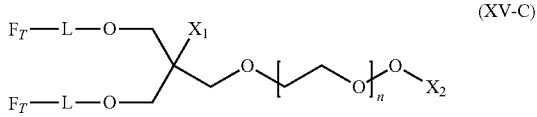

(XV-C)

where $F_T$ is a polyfluoroorgano group; L is a linker; $X_1$ is H, $CH_3$, or $CH_2CH_3$;

$X_2$ is H, $CH_3$, or $CH_2CH_3$; and n is an integer from 5 to 50.

In any of the embodiments described herein, the linker is described by formula (XVI):

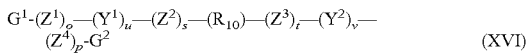

(XVI)

where $G^1$ is a bond between said polyfluoroorgano group and said linker;

$G^2$ is a bond between said linker and an oxygen atom;

$Z^1$, $Z^2$, $Z^3$, and $Z^4$ each, independently, is selected from O, S, and $NR_{11}$;

$R_{11}$ is hydrogen or a $C_{1-10}$ alkyl group;

$Y^1$ and $Y^2$ are each, independently, selected from carbonyl, thiocarbonyl, sulphonyl, or phosphoryl;

o, p, s, t, u, and v are each, independently, 0 or 1; and $R_{10}$ is a substituted or unsubstituted $C_{1-10}$ alkyl, a heteroalkyl of 1 to 10 atoms, a $C_{2-10}$ alkene, a $C_{2-10}$ alkyne, a $C_{5-10}$ aryl, a cyclic system of 3 to 10 atoms, —$(CH_2CH_2O)_q$ $CH_2CH_2$— in which q is an integer of 1 to 10, or a chemical bond linking $G^1$-$(Z^1)_o$—$(Y^1)_u$—$(Z^2)_s$— to —$(Z^3)_t$—$(Y^2)_v$—$(Z^4)_p$-$G^2$.

In some embodiments, the linker is a covalent bond or a —(C=O)— group.

In some embodiments, the composition is described by formula (XVII):

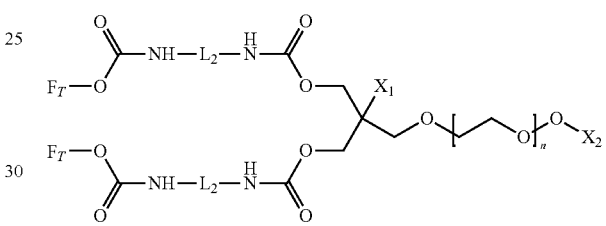

(XVII)

where $F_T$ is a polyfluoroorgano group; $L_2$ is a substituted or unsubstituted $C_{1-10}$ alkyl, a heteroalkyl of 1 to 10 atoms, a $C_{2-10}$ alkene, a $C_{2-10}$ alkyne, a $C_{5-10}$ aryl, a cyclic system of 3 to 10 atoms, —$(CH_2CH_2O)_q CH_2CH_2$— in which q is an integer of 1 to 10; $X_1$ is H, $CH_3$, or $CH_2CH_3$; $X_2$ is H, $CH_3$, or $CH_2CH_3$; and n is an integer from 5 to 50.

In some embodiments, the polyfluoroorgano group is a polyfluoroalkyl having a molecular weight of between 100-1,500 Da.

In other embodiments, the polyfluoroorgano group is a radical of the general formula $CF_3(CF_2)_rCH_2CH_2$— or $CF_3(CF_2)_s(CH_2CH_2O)_\chi$—, wherein r is an integer from 2-20, $\chi$ is an integer from 1-10, and s is an integer from 1-20.

In still other embodiments, the polyfluoroorgano group is a radical of the general formula $CH_mF_{(3-m)}(CF_2)_rCH_2CH_2$— or $CH_mF_{(3-m)}(CF_2)_s(CH_2CH_2O)_\chi$—, wherein m is 0, 1, 2, or 3; $\chi$ is an integer between 1-10; r is an integer between 2-20; and s is an integer between 1-20.

In certain embodiments, the polyfluoroorgano group is selected from $(CF_3)(CF_2)_5CH_2CH_2O$—, $(CF_3)(CF_2)_7CH_2CH_2O$—, $(CF_3)(CF_2)_5CH_2CH_2O$—, $CHF_2(CF_2)_3CH_2O$—, and $(CF_3)(CF_2)_2CH_2O$—, 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof.

In some embodiments, the composition includes a mixture of (i) any of the compositions described herein (for example, an oligofluorinated oligomer (e.g., a branched or linear oligofluorinated oligomer) or a branched compound including water insoluble segments); and (ii) a drug. In some embodiments, the drug is a hydrophobic drug (e.g., the drug is selected from antiproliferative agents and rapamycin macrolides). In some embodiments, the hydrophobic drug is an antiproliferative agent selected from methotrexate, trimetrexate, gemcitabine, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, bleomycin, and tamoxifen. In other embodiments, the hydrophobic drug is a rapamycin macrolide selected from rapamycin, CCI-779, Everolimus, and ABT-578. In other embodiments, the hydrophobic drug is paclitaxel. In some embodiments, (i):(ii) are in a ratio of 20:1 to 1:20.

In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa. In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa.

In any of the embodiments described herein, the composition further includes water. In some embodiments, the composition is an aqueous dispersion (e.g., a single or two phase dispersion).

In other embodiments, the composition is a solid dispersion.

In still other embodiments, the composition is suitable for systemic injection.

In some embodiments, the composition is in the form of liquid, tablets, capsule, powder, injectable and suppositories.

In some embodiments, the solubility of the hydrophobic drug is increased.

Any of the compositions described herein can be used in any of the methods or transient medical devices described herein.

In another aspect, the invention features a method of delivering a biologically active agent to a tissue surface in a mammalian tissue by contacting the surface with a self assembling coating including (i) an oligofluorinated oligomer (e.g., a branched or linear oligofluorinated oligomer) or a branched compound including water insoluble segments and (ii) a biologically active agent, wherein the self assembling coating resides on the tissue surface in the absence of an implanted medical device following the contacting and releases the biologically active agent to the tissue surface.

In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa. In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound including water insoluble segments can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa.

The invention also features a method of delivering a biologically active agent to a tissue surface in a mammalian tissue by contacting the surface with a transient medical device coated with a self assembling coating, the self assembling coating including (i) an oligofluorinated oligomer (e.g., a branched or linear oligofluorinated oligomer) or branched compound including water insoluble segments and (ii) a biologically active agent, wherein the transient medical device, upon the contacting, releases the biologically active agent to the tissue surface. In certain embodiments, the transient medical device is capable of disruption of the self assembling coating and, upon the disruption, releases the biologically active agent to the tissue surface. For example, the transient medical device can be a deformable transient medical device which, upon being deployed into a deformed configuration, mechanically disrupts the self assembling coating and releases the biologically active agent to the tissue surface. Alternatively, the transient medical device can be configured to direct a source of energy at the self assembling coating to disrupt the self assembling coating in response to the energy (e.g., ultrasound, heat, electromagnetic, or vibrational energy). The self assembling coating can be applied to the surface of the transient medical device by solid deposition, spray coating, printing, or dip coating. For example, the self assembling coating can be applied to the surface of the device in a two step approach; first the device is coated with the oligofluorinated oligomer (e.g., a branched or linear oligofluorinated oligomer) or branched compound including water insoluble segments and second with the biologically active agent. In some embodiments the oligofluorinated oligomer of the self assembling coating forms a self assembled layer on the transient medical device. The coating can have a thickness of from 0.01 to 250 microns (e.g., from 0.01 to 5 microns, 0.1 to 5 microns, 1 to 5 microns, 1 to 25 microns, 2 to 25 microns, 5 to 50 microns, 5 to 100 microns, 10 to 250 microns, 15 to 50 microns, or 20 to 125 microns). In particular embodiments from 5 to 55% (w/w) of the biologically active agent can be delivered from the transient medical device to the mammalian tissue (e.g., from 5 to 35%, 15 to 85%, 20 to 95%, 25 to 65%, 25 to 85%, 35 to 65%, 35 to 95%, 40 to 95%, or from 55 to 95% (w/w) of the biologically active agent is delivered). In certain embodiments that the tissue surface is in a blood vessel, the self assembling coating coats a surface of a transient medical device, and from 25 to 85% (w/w) of the biologically active agent is retained on the medical device prior to delivery to the tissue surface (e.g., from 25 to 75%, 25 to 65%, 35 to 95%, 35 to 75%, 45 to 95%, 45 to 75%, 55 to 95%, or from 55 75% (w/w) of the biologically active agent is retained). In still other embodiments, the transient medical device is folded upon itself, and from 25 to 85% (w/w) of the biologically active agent is retained on the medical device upon deploying the transient medical device from a folded to an unfolded configuration (e.g., from 25 to 75%, 25 to 65%, 35 to 95%, 35 to 75%, 45 to 95%, 45 to 75%, 55 to 95%, or from 55 75% (w/w) of the biologically active agent is retained).

In certain embodiments of the above aspects, the tissue surface is a luminal system of the mammalian tissue (e.g., a blood vessel, a vein graft, a synthetic graft, or a lumen in the respiratory, urinary, reproductive, neurologic or digestive systems). For example, the self assembling coating can be applied to the surface of a balloon catheter, inserted into a luminal system of the mammalian tissue, and deployed into an expanded configuration to transfer the biologically active agent from the surface of the balloon catheter to a tissue surface of the luminal system.

In any of the above aspects, the oligofluorinated oligomer (e.g., a branched or linear oligofluorinated oligomer) or the branched compound including water insoluble segments of the self assembling coating can be resorbable or non-resorbable. In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa. In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa.

In certain embodiments of the above aspects, the self assembling coating consists of components having a molecular weight of from 1 kDa to 60 kDa (e.g., from 1 kDa to 40 kDa, 2 kDa to 60 kDa, 2 kDa to 40 kDa, 3 kDa to 60 kDa, 3 kDa to 40 kDa, 5 kDa to 60 kDa, 5 kDa to 40 kDa, 10 kDa to 60 kDa, or from 15 kDa to 60 kDa).

In still other embodiments of the above aspects, the oligofluorinated oligomer (e.g., a branched or linear oligofluorinated oligomer) or branched compound including water insoluble segments has a theoretical molecular weight of from 1 kDa to 30 kDa (e.g., from 1 kDa to 60 kDa, 2 kDa to 60 kDa, 2 kDa to 30 kDa, 3 kDa to 60 kDa, 3 kDa to 30 kDa, 5 kDa to 60 kDa, 5 kDa to 30 kDa, 10 kDa to 60 kDa, or from 10 kDa to 30 kDa).

In particular embodiments of the above aspects, the oligofluorinated oligomer includes a hard segment, a soft segment, and polyfluoroorgano group, wherein the oligofluorinated oligomer includes from 5 to 80% (w/w) of the hard segment, from 10 to 90% (w/w) of the soft segment, and from 5 to 80% (w/w) of the polyfluoroorgano group.

In any of the above aspects, the biologically active agent can be uniformly distributed throughout the self assembling coating. In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa. In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa.

In any of the above aspects, the self assembling coating can include from 1 to 30% (w/w) fluorine atoms (e.g., from 2 to 30%, 3 to 30%, 4 to 30%, 5 to 30%, 2 to 10%, 3 to 15%, or 4 to 20% (w/w) fluorine atoms).

In any of the above aspects, the self assembling coating includes from 0.1 to 50% (w/w) biologically active agent (e.g., from 0.1 to 10%, 0.5 to 30%, 1 to 50%, 2 to 50%, 2 to 30%, 3 to 50%, 0.5 to 5%, 0.5 to 10%, 1 to 10%, 2 to 15%, 2 to 25%, 3 to 15%, or 3 to 25% (w/w) biologically active agent).

In any of the above aspects, the self assembling coating can include a molar ratio of oligofluorinated oligomer (e.g., a branched or linear oligofluorinated oligomer) or branched compound including water insoluble segments to biologically active agent of from 20:1 to 1:20 (e.g., from 1:1 to 1:20, 20:1 to 1:1, 10:1 to 1:10, 1:1 to 1:10, 10:1 to 1:1, 5:1 to 1:5, 1:1 to 1:5, or 5:1 to 1:1). In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa. In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa.

In any of the above aspects, the self assembling coating can have a glass transition of from −80 to 40° C. (e.g., from −80 to 5° C., −60 to 5° C., −50 to 20° C., −40 to 30° C., −30 to 40° C., −20 to 40° C., or −15 to 25° C.).

In any of the above aspects, the self assembling coating can have a tack of from 1.0 to 200 g (e.g., from 1.0 to 100 g, 1.0 to 50 g, 2.0 to 200 g, 2.0 to 100 g, 2.0 to 50 g, 1.0 to 25 g, 2.0 to 25 g, 3.0 to 75 g, 3.0 to 50 g, 3.0 to 25 g, or 1.0 to 20 g).

In any of the above aspects, the self assembling coating can have a viscosity of from 0.04 to 130 cps (e.g., from 20 to 130 cps, 50 to 130 cps, 75 to 130 cps, 0.04 to 30 cps, 0.04 to 70 cps, 0.5 to 130 cps, 0.5 to 13 cps, 0.5 to 30 cps, 0.5 to 70 cps, 1 to 130 cps, 1 to 20 cps, 1 to 50 cps, 5 to 25 cps, or 5 to 75 cps).

In any of the above aspects, the self assembling coating can have a contact angle hysteresis of the surface of from 20-120° (e.g., from 20-60°, 30-70°, 40-80°, 60-90°, 70-100°, 80-110°, 90-120°, 60-120°, or 35-90°).

In any of the above aspects, the biologically active agent within the coating can have a dissociation constant in phosphate buffered saline of from to 1% to 99% (e.g., from 1% to 85%, 5% to 99%, 5% to 85%, 10% to 99%, 10% to 85%, 20% to 99%, 20% to 85%, 30% to 99%, 30% to 85%, 40% to 99%, or 50% to 99%).

In any of the above aspects, the biologically active agent can be selected from proteins, peptides, carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, vitamins, lipids, and prodrugs thereof. In particular embodiments, the biologically active agent is selected from antiproliferative agents (e.g., methotrexate, trimetrexate, gemcitabine, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, bleomycin, and tamoxifen) and rapamycin macrolides (e.g., rapamycin, CCI-779, Everolimus, and ABT-578). These agents can be useful, for example, where the tissue surface is a vessel wall and the therapy is delivered to inhibit restenosis of the vessel.

In any of the above aspects, the self assembling coating can be excretable.

In any of the above aspects, the mammalian tissue can be in a subject.

In a related aspect, the invention features a transient medical device having a surface with a self assembling coating deposited thereon, the self assembling coating including (i) an oligofluorinated oligomer (e.g., a branched or linear oligofluorinated oligomer) or branched compound including water insoluble segments and (ii) a biologically active agent, wherein the transient medical device includes an energy generating element, the energy generating element being capable of disrupting the self assembling coating when activated. For example, the energy generating element can generate ultrasound, heat, electromagnetic, or vibrational energy.

In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa). In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa).

The invention further features a transient medical device having a surface with a self assembling coating deposited thereon, the self assembling coating including (i) an oligofluorinated oligomer (e.g., a branched or linear oligofluorinated oligomer) or branched compound including water insoluble segments and (ii) a biologically active agent, wherein the transient medical device is a deformable transient medical device which, upon being deployed into a deformed configuration, mechanically disrupts the self assembling coating. For example, the deformable transient medical device can be a balloon catheter.

In certain embodiments, the coating includes an oligofluorinated oligomer. The oligofluorinated oligomer can be a compound of any of Formulas (I)-(VIII), optionally having an average molecular weight of from 2 kDa to 50 KDa (e.g., from 2 kDa to 5 KDa, 4 kDa to 12 KDa, 6 kDa to 15 KDa, 5 kDa to 25 KDa, 3 kDa to 20 KDa, or from 10 kDa to 50 KDa). In certain embodiments, the oligofluorinated oligomer is a compound of formula (I), (III), (IV), (V), or (VI). The oligofluorinated oligomer can be a grafted polymer of Formula (IX). Alternatively, the oligofluorinated oligomer can be a cross linked polymer of any of Formulas (X)-(XIV). In other embodiments, the coating includes a branched compound including water insoluble segments. The branched compound can be a compound of any of Formulas (XV), (XV-A), (XV-B), (XV-C), or (XVII), optionally having an average molecular weight of from 1 kDa to 50 KDa (e.g., from 1 kDa to 5 KDa, 3 kDa to 12 KDa, 6 kDa to 15 KDa, 5 kDa to 25 KDa, 12 kDa to 40 KDa, or from 15 kDa to 50 KDa).

In any of the above transient medical devices, the coating can have a thickness of from 0.01 to 250 microns (e.g., from 0.01 to 5 microns, 0.1 to 5 microns, 1 to 5 microns, 1 to 25 microns, 2 to 25 microns, 5 to 50 microns, 5 to 100 microns, 10 to 250 microns, 15 to 50 microns, or 20 to 125 microns).

In certain embodiments of the above transient medical devices, the self assembling coating consists of components having a molecular weight of from 1 kDa to 60 kDa (e.g., from 1 kDa to 40 kDa, 2 kDa to 60 kDa, 2 kDa to 40 kDa, 3 kDa to 60 kDa, 3 kDa to 40 kDa, 5 kDa to 60 kDa, 5 kDa to 40 kDa, 10 kDa to 60 kDa, or from 15 kDa to 60 kDa).

In still other embodiments of the above transient medical devices, the oligofluorinated oligomer (e.g., a branched or linear oligofluorinated oligomer) or branched compound including water insoluble segments has a theoretical molecular weight of from 1 kDa to 30 kDa (e.g., from 1 kDa to 60 kDa, 2 kDa to 60 kDa, 2 kDa to 30 kDa, 3 kDa to 60 kDa, 3 kDa to 30 kDa, 5 kDa to 60 kDa, 5 kDa to 30 kDa, 10 kDa to 60 kDa, or from 10 kDa to 30 kDa).

In particular embodiments of the above transient medical devices, the oligofluorinated oligomer (e.g., a branched or linear oligofluorinated oligomer) or branched compound including water insoluble segments includes a hard segment, a soft segment, and polyfluoroorgano group, wherein the oligofluorinated oligomer includes from 5 to 80% (w/w) of the hard segment, from 10 to 90% (w/w) of the soft segment, and from 5 to 80% (w/w) of the polyfluoroorgano group.

In any of the above transient medical devices, the biologically active agent can be uniformly distributed throughout the self assembling coating.

In any of the above transient medical devices, the biologically active agent can be incorporated into the self assembling coating by solid deposition method.

In any of the above transient medical devices, the self assembling coating can include from 1 to 30% (w/w) fluorine atoms (e.g., from 2 to 30%, 3 to 30%, 4 to 30%, 5 to 30%, 2 to 10%, 3 to 15%, or 4 to 20% (w/w) fluorine atoms).

In any of the above transient medical devices, the self assembling coating includes from 0.1 to 50 (w/w) biologically active agent (e.g., from 0.1 to 10%, 0.5 to 30%, 1 to 50%, 2 to 50%, 2 to 30%, 3 to 50%, 0.5 to 5%, 0.5 to 10%, 1 to 10%, 2 to 15%, 2 to 25%, 3 to 15%, or 3 to 25% (w/w) biologically active agent).

In any of the above transient medical devices, the self assembling coating can include a molar ratio of oligofluorinated oligomer (e.g., a branched or linear oligofluorinated oligomer) or branched compound including water insoluble segments to biologically active agent of from 20:1 to 1:20 (e.g., from 1:1 to 1:20, 20:1 to 1:1, 10:1 to 1:10, 1:1 to 1:10, 10:1 to 1:1, 5:1 to 1:5, 1:1 to 1:5, or 5:1 to 1:1).

In any of the above transient medical devices, the self assembling coating can have a glass transition of from −80 to 40° C. (e.g., from −80 to 5° C., −60 to 5° C., −50 to 20° C., −40 to 30° C., −30 to 40° C., −20 to 40° C., or −15 to 25° C.).

In any of the above transient medical devices, the self assembling coating can have a tack of from 1.0 to 200 g (e.g., from 1.0 to 100 g, 1.0 to 50 g, 2.0 to 200 g, 2.0 to 100 g, 2.0 to 50 g, 1.0 to 25 g, 2.0 to 25 g, 3.0 to 75 g, 3.0 to 50 g, 3.0 to 25 g, or 1.0 to 20 g).

In any of the above transient medical devices, the self assembling coating can have a viscosity of from 0.04 to 130 cps (e.g., from 20 to 130 cps, 50 to 130 cps, 75 to 130 cps, 0.04 to 30 cps, 0.04 to 70 cps, 0.5 to 130 cps, 0.5 to 13 cps, 0.5 to 30 cps, 0.5 to 70 cps, 1 to 130 cps, 1 to 20 cps, 1 to 50 cps, 5 to 25 cps, or 5 to 75 cps).

In any of the above transient medical devices, the self assembling coating can have a contact angle hysteresis of the surface of from 20-120° (e.g., from 20-60°, 30-70°, 40-80°, 60-90°, 70-100°, 80-110°, 90-120°, 60-120°, or 35-90°).

In any of the above transient medical devices, the biologically active agent can be selected from proteins, peptides, carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, vitamins, lipids, and prodrugs thereof. In particular embodiments, the biologically active agent is selected from antiproliferative agents (e.g., methotrexate, trimetrexate, gemcitabine, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, bleomycin, and tamoxifen) and rapamycin macrolides (e.g., rapamycin, CCI-779, Everolimus, and ABT-578).

In any of the above transient medical devices, the self assembling coating can be excretable.

The invention further features a method for delivering a biologically active agent to a site in a vessel by including inserting into the vessel a transient medical device of the invention, positioning the transient medical device near the site, and disrupting the coating on the transient medical device deliver the biologically active agent to the site.

The invention features a method for inhibiting restenosis at a site in a vessel by inserting into the vessel a transient medical including an energy generating element and activating the energy generating element, wherein the biologically active agent is selected from antiproliferative agents and rapamycin macrolides.

The invention also features a method for inhibiting restenosis at a site in a vessel by inserting into the vessel a deformable transient medical device of the invention, and deploying the deformable transient medical device into a deformed configuration, wherein the biologically active agent is selected from antiproliferative agents and rapamycin macrolides. In certain embodiments, the deformable transient medical device is a catheter balloon. The method can further include deploying a stent at the site of disease (e.g., a stent can be deployed prior to the deployment of the catheter balloon, or deployed after deployment of the catheter balloon). The catheter balloon can be deployed for the treatment of in-stent-restenosis.

In any of the above methods for treating a vessel, the vessel can be a bifurcated vessel.

The tack of a coating of the invention can be measured, for example, using a TA.XTPlus Texture Analyser (Stable Micro Systems; distributed by Texture Technologies Corp; Scarsdale, N.Y.), which measures tack in "grams of force".

By "$C_{1-10}$ alkyl" is meant a branched or unbranched saturated hydrocarbon group, having 1 to 10 carbon atoms, inclusive. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "$C_{2-10}$ alkene" is meant a branched or unbranched hydrocarbon group containing one or more double bonds, desirably having from 2 to 10 carbon atoms. A $C_{2-10}$ alkene may optionally include monocyclic, bicyclic, or tricyclic rings, in which each ring desirably has five or six members. The $C_{2-10}$ alkene group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "$C_{2-10}$ alkyne" is meant a branched or unbranched hydrocarbon group containing one or more triple bonds, desirably having from 2 to 10 carbon atoms. A $C_{2-10}$ alkyne may optionally include monocyclic, bicyclic, or tricyclic rings, in which each ring desirably has five or six members. The $C_{2-10}$ alkyne group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

By "$C_{5-10}$ aryl" or "aryl" is meant an aromatic group having a ring system with conjugated π electrons (e.g., phenyl, or imidazole). The ring of the aryl group is preferably 5 to 10 atoms. The aromatic ring may be exclusively composed of carbon atoms or may be composed of a mixture of carbon atoms and heteroatoms. Preferred heteroatoms include nitrogen, oxygen, sulfur, and phosphorous. Aryl groups may optionally include monocyclic, bicyclic, or tricyclic rings, where each ring has preferably five or six members. The aryl group may be substituted or unsubstituted. Exemplary substituents include alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

As used herein, "C" refers to a chain terminating group. Exemplary chain terminating groups include monofunctional groups containing an amine, alcohol, or carboxylic acid functionality.

As used herein, "complexed" or "complexation" refers to an interaction, either non-covalent or via coordination to a metal center, between a complexing moiety in an oligofluorinated oligomer (e.g., a branched or linear oligofluorinated oligomer) or branched compound including water insoluble segments contained within a self assembling coating of the invention and a biologically active agent. Examples of non-covalent bonding interactions which can be used in accordance with the present invention include, without limitation, hydrogen bonding, ionic interactions (e.g., dipole-dipole interactions, ion pairing, and salt formation), inclusion complexes, clathration, van der Waals interactions (e.g., pi-pi stacking), and combinations thereof. The interaction can also be via coordination to a metal center by both the complexing moiety and the biologically active agent. In some instances, the biologically active agent includes a metal center which is coordinated to the complexing moiety.

As used herein, "complexing moiety" refers to certain embodiments of the invention including a portion of an oligofluorinated oligomer (e.g., a branched or linear oligofluorinated oligomer) or branched compound including water insoluble segments contained within a self assembling coating of the invention which complexes a biologically active agent either via a non-covalent interaction or coordination to a metal center, forming a polymer complex. The complexing moiety can be a charged moiety, e.g., a moiety which loses a proton at physiological pH thereby becoming negatively charged (e.g., carboxylate, or phosphodiester), a moiety which gains a proton at physiological pH thereby becoming positively charged (e.g., ammonium, guanidinium, or amidinium), a moiety that includes a net formal positive charge without protonation (e.g., quaternary ammonium), or a moiety that includes a net formal negative charge without loss of a proton (e.g., borate, $BR_4^-$). Exemplary charged complexing moieties include, without limitation, carboxylate, phosphodiester, phosphoramidate, borate, phosphate, phosphonate, phosphonate ester, sulfonate, sulfate, thiolate, phenolate, ammonium, amidinium, guanidinium, quaternary ammonium, and imidazolium functionalities. The complexing moiety can be designed to physically encapsulate, in whole or in part, the biologically active agent, such as a cyclodextrin. The complexing moiety can be designed to ligate a complementary oligonucleotide and/or peptide sequence present in the biologically active agent. The complexing moiety can be designed to coordinate a metal center including the biologically active agent, either as a ligand alone or including the metal center. A description of how make complexing moieties and complexation with biologically active agents is described in U.S. Patent Publication No. 20070037891, incorporated herein by reference.

As used herein, "covalently tethered" refers to moieties separated by one or more covalent bonds. For example, where an oligofluoro group is covalently tethered to an oligomer to form an oligofluorinated oligomer, tethered includes the moieties separated by a single bond as well as both moieties separated by, for example, a LinkB segment to which both moieties are covalently attached.

The term "cyclic system" refers to a compound that contains one or more covalently closed ring structures, in which the atoms forming the backbone of the ring are composed of any combination of the following: carbon, oxygen, nitrogen, sulfur, and phosphorous. The cyclic system may be substituted or unsubstituted. Exemplary substituents include, without limitation, alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

As used herein, "dissociation constant in phosphate buffered saline" refers to the equilibrium distribution of biologically active agent between a coating of the invention and phosphate buffered saline (137 mM NaCl, 2.7 mM KCl, 10 mM sodium phosphate dibasic, 2 mM potassium phosphate monobasic and a pH of 7.4) at 25° C. The dissociation constant in phosphate buffered saline is expressed as the percentage of biologically active agent present in the phosphate buffered saline solution at equilibrium and is measured by placing a coating of the invention in phosphate buffered saline and determining the equilibrium amount of biologically active agent present in the aqueous solution.

As used herein, "excretable" refers to the diffusion of oligofluorinated oligomer (e.g., a branched or linear oligofluorinated oligomer) or branched compound including water insoluble segments from the surface of a transient medical device or tissue surface coated with a self assembling coating of the invention. Excretable coatings are those in which, when dissociated from the self-assembling coatings of the invention yield only relatively small monomers capable of renal or hepatobiliary excretion without hydrolytic degradation of the oligofluorinated oligomer (e.g., a branched or linear oligofluorinated oligomer) or branched compound including water insoluble segments.

By "heteroalkyl" is meant a branched or unbranched alkyl group in which one or more methylenes ($-CH_2-$) are replaced by nitrogen, oxygen, sulfur, carbonyl, thiocarbonyl, phosphoryl, or sulfonyl moieties. Some examples include tertiary amines, ethers, thioethers, amides, thioamides, carbamates, thiocarbamates, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups As used herein, "LinkB" refers to a coupling segment capable of covalently linking or complexing oligomers, biologically active agents, and/or oligofluoro groups. Typically, LinkB molecules have molecular weights ranging from 40 to 700. Preferably the LinkB molecules are selected from the group of functionalized diamines, diisocyanates, disulfonic acids, dicarboxylic acids, diacid chlorides and dialdehydes, wherein the functionalized component has secondary functional chemistry that is accessed for chemical attachment of an oligofluoro group. Such secondary groups include, for example, esters, carboxylic acid salts, sulfonic acid salts, phosphonic acid salts, thiols, vinyls and secondary amines. Terminal hydroxyls, amines or carboxylic acids on the oligo intermediates can react with diamines to form oligo-amides; react with diisocyanates to form oligo-urethanes, oligo-ureas, oligo-amides; react with disulfonic acids to form oligo-sulfonates, oligo-sulfonamides; react with dicarboxylic acids to form oligo-esters, oligo-amides; react with diacid chlorides to form oligo-esters, oligo-amides; and react with dialdehydes to form oligo-acetal, oligo-imines.

As used herein, "inhibiting restenosis" refers to reducing the re-narrowing of arteries following treatment to clear the blockage, such as angioplasty, using a therapy of the invention in comparison to the re-narrowing that would occur following treatment to clear the blockage in the absence of any further therapy to address the risk of restenosis.

As used herein, the term "non-halogenated organic segment" refers to an organic oligomer (e.g., having a molecular weight between 100-3,500 Da) that does not include any halogen groups (i.e., F, Cl, Br, or I). The non-halogen organic segment is preferably water soluble (e.g., a polyethylene glycol).

As used herein, the term "oligofluorinated oligomer" refers to an oligomer covalently linked to an oligofluoro group. Oligofluorinated oligomers include, for example, those of any of formulas I-XIV, described herein.

By "oligo" or "oligomer" is meant a relatively short length of a repeating unit or units, generally less than about 50 monomeric units and molecular weights less than 10,000 but preferably <5,000 Daltons. Preferably, oligo is selected from the group consisting of polyurethane, polyurea, polyamides, polyalkylene oxide, polycarbonate, polyester, polylactone, polysilicone, polyethersulfone, polyolefin, polyvinyl, polypeptide, polysaccharide; and ether and amine linked segments thereof.

By "resorbable" is meant that a portion of the oligofluorinated oligomer (e.g., a branched or linear oligofluorinated oligomer) or branched compound including water insoluble segments is designed to be resorbed upon introduction into a mammalian tissue. For example, the oligomer portion of an oligofluorinated oligomer (e.g., a branched or linear oligofluorinated oligomer) or branched compound including water insoluble segments can be selected from resorbable polymers, such as polyesters (e.g., polylactic acid, polyglycolic acid, and mixtures thereof), which can be broken down and assimilated into the mammalian tissue.

As used herein, the term "trifunctional monomer" refers to a small molecule (e.g., having a molecular weight between 50-3500 Da) that includes three functional groups that can form covalent bonds to another compound (e.g., any of the linkers described herein). Exemplary trifunctional monomers include triols, tricarboxylic acids and acid derivatives, and triisocyanates. Trifunctional monomers that can be used in the compositions, methods, and transient medical devices described herein include glycerol, trimethylolpropane (TMP), trimethylolethane (TME), trimesic acid (TMA), tris(hydroxyethyl)isocyanurate (THEIC), pentaerythritol, pyromellitic acid, 1,3,5-trihydroxybenzene, triamino pyrimidine, or melamine.

As used herein, the term "transient medical device" refers to a device that is designed to reside only temporarily within the body or mammalian tissue (e.g., only during the performance of a medical procedure and/or delivery of a biologically active agent to a target tissue). The transient medical device is removed within 30 minutes after the biologically active agent is delivered to the tissue being treated.

As used herein, the term "water insoluble segment" refers to an organic oligomeric segment (e.g., having a molecular weight between 200-3,500 or 100-1,500 Da) that is not miscible in water. Exemplary water insoluble segments include the polyfluoroorganic segments described herein, as well as polysiloxane or polyolefins and other oligomers described herein.

Other features and advantages of the invention will be apparent from the following Detailed Description, the Drawings, and the Claims.

DETAILED DESCRIPTION

Figure 1:
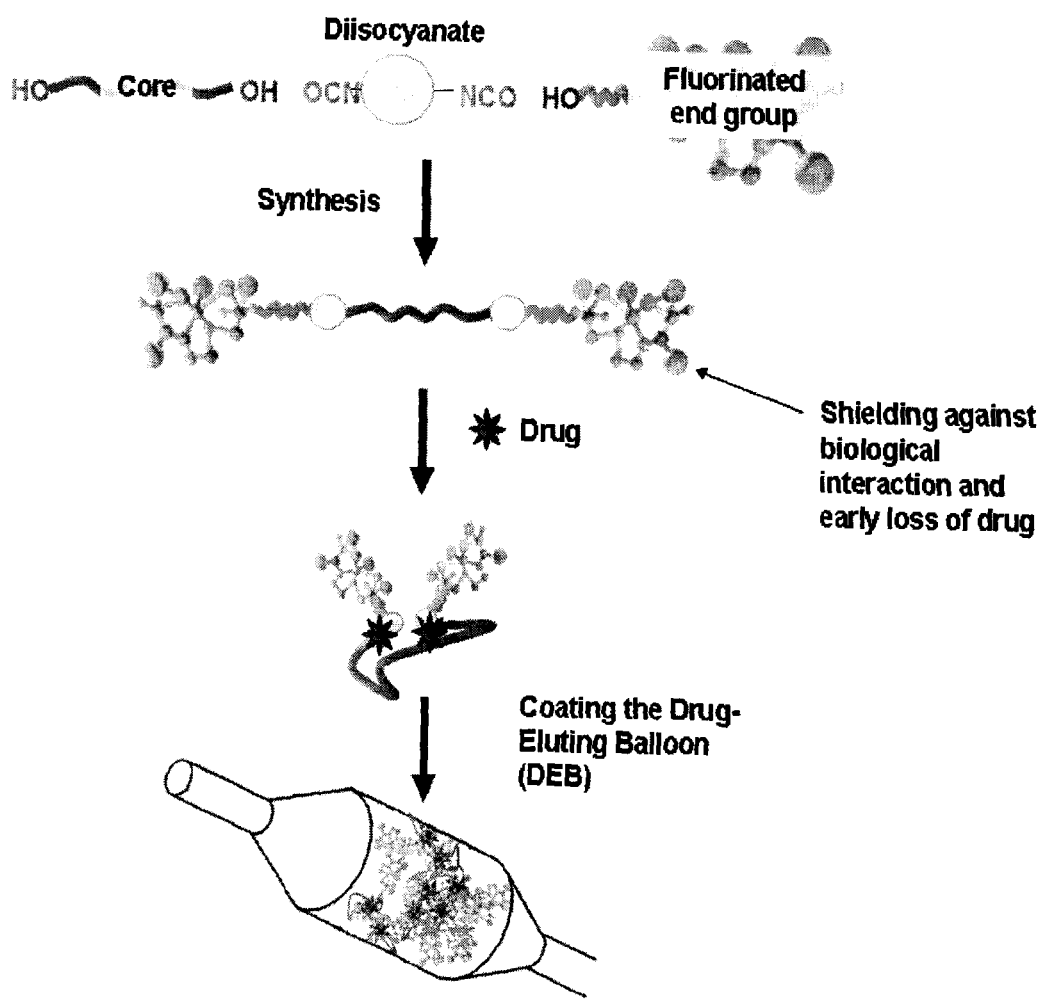
FIG. 1 is an illustration depicting a fluorinated drug delivery composition and angioplasty balloon coating. The fluorodomain provides a shield limiting solubility (because of its inherent water repelling character) during the delivery of the pharmaceutical complex (covalent and non-covalent) to the diseased tissue. The chemistry of non-fluorinated segments can be selected in such manner to yield good binding to the balloon surface during the transfer to the diseased tissue.
Figure 2:
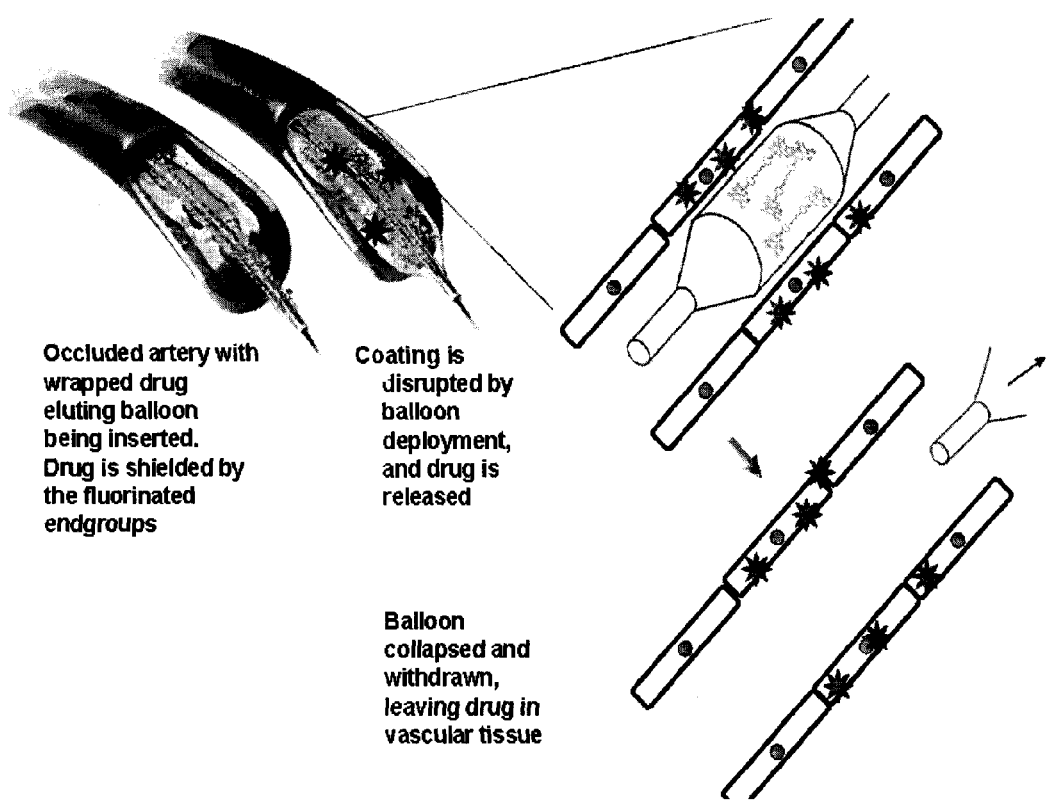
FIG. 2 is an illustration depicting the deployment of a coated balloon in an occluded vessel. In the second picture frame, the delivery molecules have lost their ability to form a continuous film because of balloon expansion at the diseased tissue site, thereby resulting in separation of the drug from the oligofluorinated molecules which are now beginning to hydrate at the drug binding site. In the third picture frame, the delivery molecule is no longer observed because it has dissolved into the blood stream where it can be eliminated via the renal system.

The methods and compositions of the invention feature a self assembling coating or formulation including an oligomeric compound (for example, an oligofluorinated oligomer, e.g., a branched or linear oligofluorinated oligomer, or branched compound including water insoluble segments), preferably a branched compound, and a biologically active agent. The biologically active agent can be incorporated within the coating or formulation in a variety of ways, including via non-covalent complexation with an oligofluorinated oligomer bearing a complexing moiety (e.g., incorporated into LINKB, oligo, or $F_T$), via covalent linkage to an oligofluorinated oligomer, as a physical inclusion.

The coatings and formulations of the invention are conveniently formed by the self assembly of oligomeric compounds (for example, oligofluorinated oligomers, e.g., branched or linear oligofluorinated oligomers, or branched compound including water insoluble segments), preferably a branched compound, which include a core oligomer, a water insoluble segment (e.g., a fluorinated segment), and, optionally, a co-localization site for a biologically active agent. The coatings and formulations can have good blood compatibility (low blood activating), and can be excretable (easily eliminated from the body and without localization which can lead to reduce chronic local inflammation). The central core allows the delivery platform to bind to a polymeric or metallic interventional device. The water insoluble segment (e.g., the fluorinated segment) is critical to minimizing blood activation in a flowing blood environment, for shielding the biologically active agent from environmental challenges (e.g., degradation and premature release of the agent, either as a result of dissolution prior to reaching the site of treatment, or loss due to tackiness in devices that fold, unfold or change shape during delivery) until delivered to the diseased tissue site, and for self assembly of the oligomeric compound (e.g., oligofluorinated oligomer), preferably branched, into a self assembling coating for containing the biologically active agent. The optional biologically active agent binding site allows for compatibility of the delivery system with a wide variety of different therapeutic agents. The excretable feature of the self assembling coating and formulation is part of a strategy to allow simple dissolution and elimination of the carrier molecule, rather than retention or release of in-situ degradation products that lead to the pro-inflammatory events characteristic of certain drug eluting stents (see Virmani R, Semin Interv Cardiol 3(3-4):163 (1998); Ross et al., Adv Exp Med Biol 102:135 (1978); and Barker S G, Atherosclerosis 105(2):131 (1994)).

Oligofluorinated Oligomers and Branched Compounds Including Water Insoluble Segments Oligofluorinated Oligomers and Polyfluoroorganic Groups Oligofluorinated oligomers include an oligo covalently linked to an oligofluoro group and can be described, without limitation, by any of formulas I-XIV.

The oligofluorinated oligomer can be a polymer described by formula (I):

$$F_T\text{-(oligo)-}F_T \qquad (I),$$

wherein $F_T$ is a polyfluoroorgano group and oligo is an oligomeric segment.

The oligofluorinated oligomer can be a polymer described by formula (II):

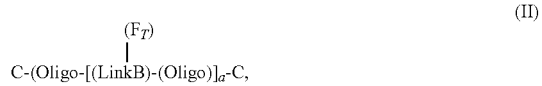

$$\begin{array}{c} (F_T) \\ | \\ C\text{-(Oligo-[(LinkB)-(Oligo)]}_a\text{-C,} \end{array} \qquad (II)$$

wherein (i) $F_T$ is a polyfluoroorgano group covalently attached to LinkB, (ii) C is a chain terminating group, (iii) Oligo is an oligomeric segment, (iv) LinkB is a coupling segment, and (v) a is an integer greater than 0 (e.g., an integer from 1 to 50, 1 to 20, or 1 to 10).

The oligofluorinated oligomer can be a polymer described by formula (III):

$$F_T\text{—[B-(oligo)]-B—}F_T \qquad (III),$$

wherein B includes a urethane; oligo is an oligomeric segment; $F_T$ is a polyfluoroorgano group; and n is an integer from 1 to 10.

In formulas (I), (II), and (III), the oligo can be a branched or non-branched oligomeric segment of form 1 to 50 repeating units, such as an oligomeric segment including polyurethane, polyurea, polyamides (including polypeptides), polyalkylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide (including neopentylglycol, among other polypropylene oxide derivatives), polyethylene oxide, polytetramethyleneoxide, or polyethylenebutylene segments. In particular embodiments, the oligo includes polypropylene oxide, polyethylene oxide, or polytetramethyleneoxide.

The oligofluorinated oligomer can be a polymer described by formula (IV):

$$F_T-[B-A]_n-B-F_T \quad (IV),$$

wherein (i) A is a soft segment including hydrogenated polybutadiene, poly(2,2 dimethyl-1-3-propylcarbonate), polybutadiene, poly(diethylene glycol)adipate, poly(hexamethylene carbonate), poly(ethylene-co-butylene), neopentyl glycol-ortho phthalic anhydride polyester, diethylene glycol-ortho phthalic anhydride polyester, 1,6-hexanediol-ortho phthalic anhydride polyester, or bisphenol A ethoxylate; (ii) B is a hard segment including a urethane; (iii) $F_T$ is a polyfluoroorgano group; and (iv) n is an integer from 1 to 10. For example, the hard segment can be formed from a diisocyanate selected from 3-isocyanatomethyl, 3,5,5-trimethyl cyclohexylisocyanate; 4,4'-methylene bis(cyclohexyl isocyanate); 4,4'-methylene bis(phenyl) isocyanate; toluene-2,4 diisocyanate); m-tetramethylxylene diisocyanate; and hexamethylene diisocyanate; and n can be 1 or 2.

The oligofluorinated oligomer can be a polymer described by formulas (V) or (VI):

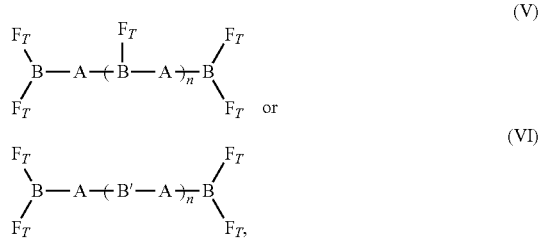

wherein (i) A is a soft segment; (ii) B is a hard segment including a isocyanurate trimer or biuret trimer; (iii) B' is a hard segment including a urethane; (iv) each $F_T$ is a polyfluoroorgano group; and (v) n is an integer between 0 to 10. soft segment can have a number average molecular weight (Mn), of 500 to 3,500 Daltons and include hydrogenated polybutadiene (HLBH), poly(2,2 dimethyl-1-3-propylcarbonate) (PCN), polybutadiene (LBHP), polytetramethylene oxide (PTMO), diethyleneglycol-orthophthalicanhydride polyester (PDP), hydrogenated polyisoprene (HHTPI), poly(hexamethylene carbonate), poly(2-butyl-2-ethyl-1,3-propyl carbonate), or hydroxylterminated polydimethylsiloxanes block copolymer (C22). The hard segment can be formed by reacting a triisocyanate with a diol including the soft segment, wherein the triisocyanate is selected from hexamethylene diisocyanate (HDI) biuret trimer, isophorone diisocyanate (IPDI) trimer, or hexamethylene diisocyanate (HDI) trimer.

Alternatively, the coatings of the invention include a biologically active agent covalently tethered or complexed to the oligofluorinated oligomer. Such an oligofluorinated oligomer can be described by formula (VII):

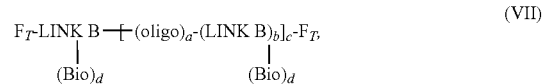

$$F_T\text{-LINK B}\underset{\underset{(\text{Bio})_d}{|}}{\text{-}}[\text{(oligo)}_a\text{-(LINK B)}_b]_c\text{-}F_T, \quad (VII)$$

wherein oligo is an oligomeric segment; Bio is a biologically active agent; $F_T$ is an oligofluoro group; each Link B is, independently, an organic moiety covalently bound to oligo, $F_T$, or Bio; a is an integer greater than 0 (e.g., 1-50, 1-20, 1-10, or 1-5); b and c are each, independently, integers greater than or equal to 0 (e.g., 1-20, 1-10, 1-5, 2-20, 2-10, or 2-5); and d is 0 or 1. The oligomer can include a polyurethane, polyurea, polyamides, polyalkylene oxide, polycarbonate, polyester, polylactone, polysilicone, polyethersulfone, polyolefin, polyvinyl, polypeptide, polysaccharide, or combinations thereof.

In certain coatings, the self assembling coating is formed from oligofluorinated oligomers including a non-terminal polyfluoroorgano group, such as those of formula (VIII):

$$C\text{-(LinkB)-}[F_T\text{-(LinkB)}]_a\text{-C} \quad (VIII),$$

wherein (i) $F_T$ is a difunctional polyfluoroorgano group covalently attached at both ends to LinkB; (ii) C is a chain terminating group; (iii) LinkB is a coupling segment; and (iv) a is an integer greater than 0 (e.g., 1-50, 1-20, 1-20, 1-5, 2-20, 2-10, or 3-20).

The self assembling coating can be formed from a grafted polymer described by formula (IX):

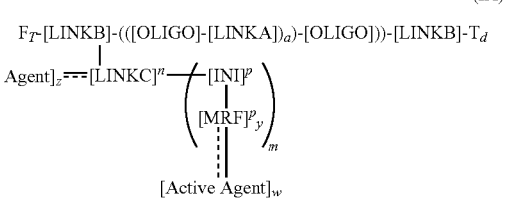

(IX)

wherein [OLIGO] is an oligomeric polymeric segment; [LINKA] is a first coupling segment linking at least two [OLIGO] groups to form ((([OLIGO]-[LINKA])$_a$[OLIGO])) having a theoretical molecular weight of less than 15,000 Da; T is a terminal group; $F_T$ is a polyfluoroorgano group; [MRF] is a polyolefin; [INI] is a functional group having the capacity to initiate ATRP, atom transfer radical addition (ATRA), or atom transfer radical cyclization (ATRC); [LINKB] is a second coupling segment linking ((([OLIGO]-[LINKA])$_a$[OLIGO])) to $F_T$, to T, and/or to [LINKC]; [LINKC] is a third coupling segment linking [LINKB] to [INI] or, in the absence of [INI], [LINKC] is a dendron of n generations; [Active Agent] is one or more biologically active agents either complexed or covalently tethered to [LINKC] or to [MRF]; each of a and d are, independently, integers greater than 0 (e.g., 1-20, 1-10, or 1-5), n is an integer from 1 to 150 (e.g., 1-50, 1-20, 1-10, or 1-5); p is an integer from 1 to 20 (e.g., 1-10, 1-5, or 2-10); and each of m, p, y, and w are, independently, 0 or an integer from 1 to 20 (e.g., 1-10, 1-5, or 2-10); with the provisos that m≤n, w≤y, when m, p, y, and w are 0, then n is an integer from 2 to 150, when z≥1, then m=0, and when m≥1, then z=0. The portion ((([OLIGO]-[LINKA])$_a$-[OLIGO])) can include a polycondensate selected from polyurethane, polyurea, polyamides, polyalkylene oxide, polycarbonate, polyester, polylactone, polysilicone, polyethersulfone, polypeptide, polysaccharide, polysiloxane, polydimethylsiloxane, polypropylene oxide, polyethylene oxide, polytetramethyleneoxide, and combinations thereof. The portion [MRF] can be selected from polyacrylic acid, polymethacrylic acid, poly(hydroxyethylmethacrylate), poly(hydroxyethylacrylate), poly(methylalkylsulfoxide methacrylate), poly(methylalkylsulfoxide acrylate), polyacrylamide, poly(methacrylamide), poly(dimethylacrylamide), poly(N-isopropyl-acrylamide), poly(vinyl alcohol), poly(vinyl pyrrolidone), poly(N-vinyl caprolactam), and copolymers thereof. The portion oligo or oligomer can include, without limitation, polyurethanes, polyureas, polyamides, polyalkylene oxides, polycarbonates, polyesters, polylactones, polysilicones, polyethersulfones, polyolefins, polyvinyl derivatives, polypeptides, polysaccharides, polysiloxanes, polydimethylsiloxanes, polyethylene-butylene, polyisobutylenes, polybutadienes, polypropylene oxides, polyethylene oxides, polytetramethyleneoxides, polyethylenebutylenes, polycaprolactone, polylactic, polyethylene glycol, polypropylene glycol, polydiethyleneglycol phthalate, polydiethyleneglycol adipate, polyhydroxybutyrate, polyhydroxyoctanoate, polyhydroxyvalerate, biOH™ soybean oil-derivative (Cargill), and combinations and mixtures thereof.

The self assembling coating can be a polymerized coating formed from a monomer including (i) two or more cross-linking domains, and (ii) an oligomeric segment having a first end covalently tethered to a first cross-linking domain and a second end covalently tethered to a second cross-linking domain, wherein at least one of the cross-linking domains is an oligofluorinated cross-linking domain. The monomer can further be described by formula (I):

(D)-[(oligo)-(D)]$_n$     (X), in which oligo is an oligomeric segment; each D is a cross-linking domain; and n is an integer from 1 to 20, 1 to 15, 1 to 10, 1 to 8, or 1 to 5, and wherein at least one D is an oligofluorinated cross-linking domain. Alternatively, the monomer can further be described by formula (XI):

(D)-[(oligo)-(LinkA-F$_T$)]$_m$-[(oligo)-(D)]$_n$     (XI), in which oligo is an oligomeric segment; each D is a cross-linking domain; F$_T$ is an oligofluoro group; each LinkA-F$_T$ is an organic moiety covalently bound to a first oligo, a second oligo, and F$_T$; n is an integer from 1 to 20 (e.g., 1-10, 1-5, or 2-10); and m is an integer from 1 to 20 (e.g., 1-10, 1-5, or 2-10), wherein at least one D is an oligofluorinated cross-linking domain. Cross-linking domains which can be utilized in the preparation of coatings of the invention include a reactive moiety that capable of chain growth polymerization, such as, without limitation, vinyls, epoxides, aziridines, and oxazolines. For example, the cross-linking domain is selected from

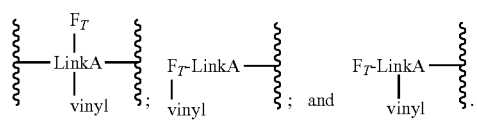

The monomer can further be described by formula (XII):

(oligo)$_n$(vinyl)$_m$(F$_T$)$_o$     (XII), in which oligo is an oligomeric segment; vinyl is a cross-linking domain including an unsaturated moiety capable of undergoing radical initiated polymerization; F$_T$ is an oligofluoro group covalently tethered to the vinyl and/or the oligo; and each of n, m, and o is, independently, an integer from 1 to 5, wherein the monomer includes at least one oligofluorinated cross-linking domain. The monomer may further be described by formula (XIII):

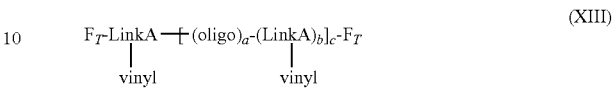

(XIII)

in which oligo is an oligomeric segment; vinyl is a cross-linking domain including an unsaturated moiety capable of undergoing radical initiated polymerization; F$_T$ is an oligofluoro group; each LinkA is, independently, an organic moiety covalently bound to oligo, F$_T$, and vinyl; and each of a, b, and c are, independently, integers greater than 0 (e.g., 1-20, 1-10, 1-5, 2-10, or 2-5). The polymerized coating can be prepared by mixing the monomer bearing cross linking domains with a nonfluorinated vinyl compound, such as acrylic acid, methyl acrylate, ethyl acrylate, n-butyl acrylate, 2-hydroxyethyl acrylate, n-butyl acrylate, glycidyl acrylate, vinyl acrylate, allyl acrylate, 2-hydroxyethyl acrylate, 2-hydroxy ethyl methacrylate (HEMA), 2-amino ethyl methacrylate, glycerol monomethacrylate, acrylamide, methacrylamide, N-(3-aminopropyl)methacrylamide, crotonamide, allyl alcohol, or 1,1,1-trimethylpropane monoallyl ether.

The self assembling coating can be a polymerized coating formed from a monomer including (i) a first component having a core substituted with m nucleophilic groups, where m≥2; and a second component having a core substituted with n electrophilic groups, where n≥2 and m+n>4; wherein the composition includes at least one oligofluorinated nucleophilic group or one oligofluorinated electrophilic group, and wherein the first component and the second component react to form oligofluorinated cross-linked polymer. The monomer may further be described by formula (XIV):

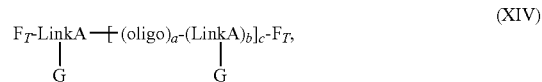

(XIV)

in which oligo is an oligomeric segment; G is either a nucleophilic group or an electrophilic group; F$_T$ is an oligofluoro group; each LinkA is, independently, an organic moiety covalently bound to oligo, F$_T$, and G; and each of a, b, and c are, independently, integers greater than 0 (e.g., 1-20, 1-10, 1-5, 2-10, or 2-5). To form the polymerized coating the nucleophilic groups and the electrophilic groups undergo a nucleophilic substitution reaction, a nucleophilic addition reaction, or both upon mixing. The nucleophilic groups can be selected from, without limitation, primary amines, secondary amines, thiols, alcohols, and phenols. The electrophilic groups can be selected from, without limitation, carboxylic acid esters, acid chloride groups, anhydrides, isocyanato, thioisocyanato, epoxides, activated hydroxyl groups, succinimidyl ester, sulfosuccinimidyl ester, maleimido, and ethenesulfonyl. Desirably, the number of nucleophilic groups in the mixture is approximately equal to the number of electrophilic groups in the mixture (i.e., the ratio of moles of nucleophilic groups to moles of electrophilic groups is about 2:1 to 1:2, or even about 1:1).

In any of the above formulas the oligofluoro group, $F_T$, can be a polyfluoroalkyl having a molecular weight of between 100-1,500 Da. For example, $F_T$ can be selected from the group consisting of radicals of the general formula $CF_3(CF_2)_rCH_2CH_2$— wherein r is 2-20, and $CF_3(CF_2)_sCH_2CH_2O)_\chi$ wherein $\chi$ is 1-10 and s is 1-20; or $F_T$ can be selected from the group consisting of radicals of the general formula $CH_mF_{(3-m)}(CF_2)_rCH_2CH_2$— and $CH_mF_{(3-m)}(CF_2)_s(CH_2CH_2O)_\chi$—, wherein m is 0, 1, 2, or 3; $\chi$ is an integer between 1-10; r is an integer between 2-20; and s is an integer between 1-20. In any of the above formulas, $F_T$ can be selected from $(CF_3)(CF_2)_5CH_2CH_2O$—, $(CF_3)(CF_2)_2CH_2CH_2O$—, $(CF_3)(CF_2)_5CH_2CH_2O$—, $CHF_2(CF_2)_3CH_2O$—, and $(CF_3)(CF_2)_2CH_2O$—, 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof.

The amount of biologically active agent loaded into the coating will depend upon the design of the oligomer in combination with the desired release profile. The oligomer may be designed for the particular agent being delivered and to provide the biocompatibility necessary for a particular application.

In general, oligofluorinated oligomers used in the methods and compositions of the invention, and those described by formulas I-XIV can be prepared as described in U.S. Pat. Nos. 6,127,507, and 6,770,725; PCT Publication Nos. WO20007/004067, WO2007/148230, WO2008/076345, and WO2009/043174; and PCT Application No. PCT/US2009/55418, filed on Aug. 28, 2009, each of which is incorporated herein by reference.

Branched Compounds Including Water Insoluble Segments

Branched compounds including water insoluble segments include compounds described by any of formulas (XV), (XV-A), (XV-B), (XV-C), and (XVII).

The branched compound can be a compound of formula (XV):

(XV)

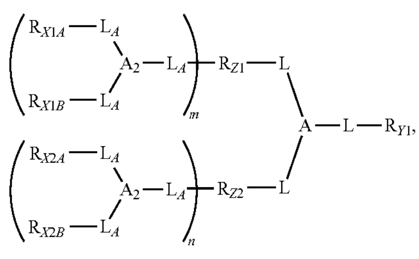

wherein m and n are both 0, or m and n are both 1; each A and $A_2$ is a trifunctional monomer having a molecular weight between 50-300 Da; each L and $L_A$ is, independently, a linker; each $R_{X1A}$, $R_{X1B}$, $R_{X2A}$, and $R_{X2B}$ is, independently, a water insoluble segment having a molecular weight between 100-1,500 Da; and $R_{Y1}$ is a non-halogenated organic segment having a molecular weight between 100-1,500 Da; and when m and n are both 1, each of $R_{Z1}$ and $R_{Z2}$ is, independently, a difunctional water insoluble segment having a molecular weight between 50-800 Da, or when m and n are both 0, each of $R_{Z1}$ and $R_{Z2}$ is, independently a water insoluble segment having a molecular weight between 100-1,500 Da.

The branched compound can be a compound of formula (XV-A):

(XV-A)

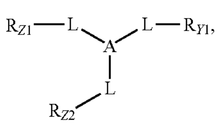

wherein A is a trifunctional monomer having a molecular weight between 50-300 Da; each L is, independently, a linker; $R_{Z1}$ and $R_{Z2}$ are each, independently, an organohalide segment having a molecular weight between 100-1,500 Da; and $R_{Y1}$ is a non-halogenated organic segment having a molecular weight between 100-1,500 Da. In some embodiments, $R_{Z1}$ and $R_{Z2}$ are fluorinated diols.

The branched compound can be a compound of formula (XV-B):

(XV-B)

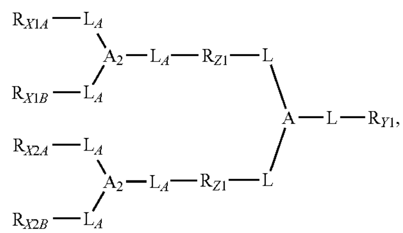

wherein each of A, $A_2$, L, $L_A$, $R_{X1A}$, $R_{X1B}$, $R_{X2A}$, $R_{X2B}$, $R_{Y1}$, $R_{Z1}$, and $R_{Z2}$ are defined as described in Formula (XV).

For example, in any of formulas (XV), (XV-A), or (XV-B), A can be derived from a triol, or a trifunctional moiety selected from, e.g., glycerol, trimethylolpropane (TMP), trimethylolethane (TME), trimesic acid (TMA), or tris(hydroxyethyl)isocyanurate (THEIC). In certain embodiments, $R_{Y1}$ is a linear or branched polyethylene glycol, a zwitterions (including zwitterionic surfactant moieties, e.g., alkyl betaines, such as alkyl amidopropyl betaine, sulfobetaines and alkyl sultaines, alkyl ether hydroxylpropyl sultaines, and alkylamidopropylhydroxy sultaines), or polyvinylpyrrolidone. In other embodiments, $R_{Z1}$ and $R_{Z2}$ are each, independently, a polyfluoroorgano group, or wherein each of $R_{X1A}$, $R_{X1B}$, $R_{X2A}$, $R_{X2B}$ are each, independently, a polyfluoroorgano group. In still other embodiments, $R_{Z1}$ and $R_{Z2}$ are each, independently, a silicone group, or wherein each of $R_{X1A}$, $R_{X1B}$, $R_{X2A}$, $R_{X2B}$ are each, independently, a silicone group.

The branched compound including water insoluble segments can be a compound of formula (XV-C):

(XV-C)

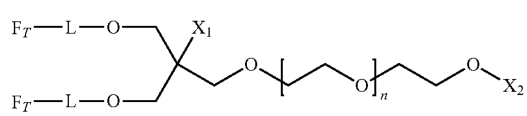

wherein $F_T$ is a polyfluoroorgano group; L is a linker; $X_1$ is H, $CH_3$, or $CH_2CH_3$;

$X_2$ is H, $CH_3$, or $CH_2CH_3$; and n is an integer from 5 to 50.

The linker of the branched compound including water insoluble segments can be described by formula (XVI):

$$G^1\text{-}(Z^1)_o\text{—}(Y^1)_u\text{—}(Z^2)_s\text{—}(R_{10})\text{—}(Z)_t\text{—}(Y^2)_v\text{—}(Z^4)_p\text{-}G^2 \quad \text{(XVI)}$$

wherein $G^1$ is a bond between said polyfluoroorgano group and said linker; $G^2$ is a bond between said linker and an oxygen atom; $Z^1$, $Z^2$, $Z^3$, and $Z^4$ each, independently, is selected from O, S, and $NR_{11}$; $R_{11}$ is hydrogen or a $C_{1-10}$ alkyl group; $Y^1$ and $Y^2$ are each, independently, selected from carbonyl, thiocarbonyl, sulphonyl, or phosphoryl; o, p, s, t, u, and v are each, independently, 0 or 1; and $R_{10}$ is a substituted or unsubstituted $C_{1-10}$ alkyl, a heteroalkyl of 1 to 10 atoms, a $C_{2-10}$ alkene, a $C_{2-10}$ alkyne, a $C_{5-10}$ aryl, a cyclic system of 3 to 10 atoms, —(CH$_2$CH$_2$O)$_q$CH$_2$CH$_2$— in which q is an integer of 1 to 10, or a chemical bond linking G$^1$-(Z$^1$)$_o$—(Y$^1$)$_u$—(Z$^2$)$_s$— to —(Z$^3$)$_t$—(Y$^2$)$_v$—(Z$^4$)$_p$-G$^2$. In certain embodiments, the linker is a covalent bond or a —(C=O)— group.

The branched compound including water insoluble segments can be a compound of formula (XVII):

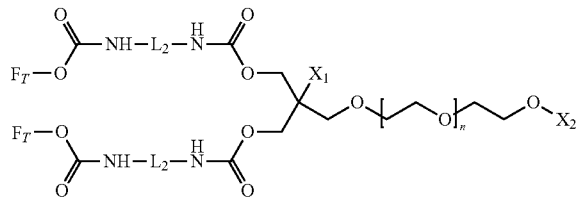

(XVII)

wherein F$_T$ is a polyfluoroorgano group; L$_2$ is a substituted or unsubstituted C$_{1-10}$ alkyl, a heteroalkyl of 1 to 10 atoms, a C$_{2-10}$ alkene, a C$_{2-10}$ alkyne, a C$_{5-10}$ aryl, a cyclic system of 3 to 10 atoms, —(CH$_2$CH$_2$O)$_q$CH$_2$CH$_2$— in which q is an integer of 1 to 10; X$_1$ is H, CH$_3$, or CH$_2$CH$_3$; X$_2$ is H, CH$_3$, or CH$_2$CH$_3$; and n is an integer from 5 to 50. In certain embodiments, the polyfluoroorgano group is a polyfluoroalkyl having a molecular weight of between 100-1,500 Da. In other embodiments, the polyfluoroorgano group is a radical of the general formula CF$_3$(CF$_2$)$_r$CH$_2$CH$_2$— or CF$_3$(CF$_2$)$_s$(CH$_2$CH$_2$O)$_\chi$—, wherein r is an integer from 2-20, $\chi$ is an integer from 1-10, and s is an integer from 1-20. In still other embodiments, the polyfluoroorgano group is a radical of the general formula CH$_m$F$_{(3-m)}$(CF$_2$)$_r$CH$_2$CH$_2$— or CH$_m$F$_{(3-m)}$(CF$_2$)$_s$(CH$_2$CH$_2$O)$_\chi$—, wherein m is 0, 1, 2, or 3; x is an integer between 1-10; r is an integer between 2-20; and s is an integer between 1-20. In certain embodiments, the polyfluoroorgano group is selected from (CF$_3$)(CF$_2$)$_5$CH$_2$CH$_2$O—, (CF$_3$)(CF$_2$)$_7$CH$_2$CH$_2$O—, (CF$_3$)(CF$_2$)$_5$CH$_2$CH$_2$O—, CHF$_2$(CF$_2$)$_3$CH$_2$O—, and (CF$_3$)(CF$_2$)$_2$CH$_2$O—, 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof.

Water Insoluble Segments

The branched compounds described herein (e.g., compositions of Formulas (XV), (XV-A), (XV-B), (XV-C), and (XVII)) include water insoluble segments. Exemplary water insoluble segments include polyfluoroorgano groups (e.g., the F$_T$ groups described herein), polysulfones, aromatic polyimides, and amides. Others include polysiloxanes, polyolefins such as C10, C12 and other saturated or unsaturated hydrocarbons.

Linkers

The branched compound including water insoluble segments described herein (e.g., compositions of Formulas (XV), (XV-A), (XV-B), (XV-C), and (XVII)) include linkers. The linker component of the invention is, at its simplest, a bond between the trifunctional monomer and the organohalide segment (e.g., a polyfluoroorgano group) or the non-halogenated organic segment. The linker can be a linear, cyclic, or branched molecular skeleton, optionally having pendant groups.

Thus, the linking of the trifunctional monomer and the organohalide segment (e.g., a polyfluoroorgano group) or the non-halogenated organic segment is achieved by covalent means, involving bond formation with one or more functional groups located on each group. Examples of chemically reactive functional groups which may be employed for this purpose include, without limitation, amino, hydroxyl, sulfhydryl, carboxyl, carbonyl, carbohydrate groups, vicinal diols, thioethers, 2-aminoalcohols, 2-aminothiols, guanidinyl, imidazolyl, and phenolic groups.

The covalent linking of the trifunctional monomer and the organohalide segment (e.g., a polyfluoroorgano group) or the non-halogenated organic segment may be effected using a linker which contains reactive moieties capable of reaction with such functional groups present in the trifunctional monomer and the organohalide segment or the non-halogenated organic segment. For example, a hydroxyl group of the trifunctional monomer may react with a carboxyl group of the linker, or an activated derivative thereof, resulting in the formation of an ester linking the two.

Examples of moieties capable of reaction with sulfhydryl groups include α-haloacetyl compounds of the type XCH$_2$CO— (where X=Br, Cl or I), which show particular reactivity for sulfhydryl groups, but which can also be used to modify imidazolyl, thioether, phenol, and amino groups as described by Gurd, *Methods Enzymol.* 11:532 (1967). N-Maleimide derivatives are also considered selective towards sulfhydryl groups, but may additionally be useful in coupling to amino groups under certain conditions. Reagents such as 2-iminothiolane (Traut et al., *Biochemistry* 12:3266 (1973)), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type XCH$_2$CO— (where X=Cl, Br or I), for example, as described by Wong *Biochemistry* 24:5337 (1979);

(ii) N-maleimide derivatives, which may react with amino groups either through a Michael type reaction or through acylation by addition to the ring carbonyl group, for example, as described by Smyth et al., *J. Am. Chem. Soc.* 82:4600 (1960) and *Biochem. J.* 91:589 (1964); (iii) aryl halides such as reactive nitrohaloaromatic compounds; (iv) alkyl halides, as described, for example, by McKenzie et al., *J. Protein Chem.* 7:581 (1988); (v) aldehydes and ketones capable of Schiff's base formation with amino groups, the adducts formed usually being stabilized through reduction to give a stable amine; (vi) epoxide derivatives such as epichlorohydrin and bisoxiranes, which may react with amino, sulfhydryl, or phenolic hydroxyl groups; (vii) chlorine-containing derivatives of s-triazines, which are very reactive towards nucleophiles such as amino, sulfhydryl, and hydroxyl groups; (viii) aziridines based on s-triazine compounds detailed above, e.g., as described by Ross, *J. Adv. Cancer Res.* 2:1 (1954), which react with nucleophiles such as amino groups by ring opening; (ix) squaric acid diethyl esters as described by Tietze, *Chem. Ber.* 124:1215 (1991); and (x) α-haloalkyl ethers, which are more reactive alkylating agents than normal alkyl halides because of the activation caused by the ether oxygen atom, as described by Benneche et al., *Eur. J. Med. Chem.* 28:463 (1993).

Representative amino-reactive acylating agents include: (i) isocyanates and isothiocyanates, particularly aromatic derivatives, which form stable urea and thiourea derivatives respectively; (ii) sulfonyl chlorides, which have been described by Herzig et al., *Biopolymers* 2:349 (1964); (iii) acid halides; (iv) active esters such as nitrophenylesters or N-hydroxysuccinimidyl esters; (v) acid anhydrides such as mixed, symmetrical, or N-carboxyanhydrides; (vi) other useful reagents for amide bond formation, for example, as described by M. Bodansky, Principles of Peptide Synthesis, Springer-Verlag, 1984; (vii) acylazides, e.g. wherein the azide group is generated from a preformed hydrazide derivative using sodium nitrite, as described by Wetz et al., *Anal. Biochem.* 58:347 (1974); and (viii) imidoesters, which form stable amidines on reaction with amino groups, for example, as described by Hunter and Ludwig, *J. Am. Chem. Soc.* 84:3491 (1962). Aldehydes and ketones may be reacted with amines to form Schiff's bases, which may advantageously be stabilized through reductive amination. Alkoxylamino moieties readily react with ketones and aldehydes to produce stable alkoxamines, for example, as described by Webb et al., in *Bioconjugate Chem.* 1:96 (1990).

Examples of reactive moieties capable of reaction with carboxyl groups include diazo compounds such as diazoacetate esters and diazoacetamides, which react with high specificity to generate ester groups, for example, as described by Herriot, *Adv. Protein Chem.* 3:169 (1947). Carboxyl modifying reagents such as carbodiimides, which react through O-acylurea formation followed by amide bond formation, may also be employed.

It will be appreciated that functional groups in the trifunctional monomer and the organohalide segment or the non-halogenated organic segment may, if desired, be converted to other functional groups prior to reaction, for example, to confer additional reactivity or selectivity. Examples of methods useful for this purpose include conversion of amines to carboxyls using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxyls using reagents such as α-haloacetates; conversion of thiols to amines using reagents such as ethylenimine or 2-bromoethylamine; conversion of carboxyls to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of the trifunctional monomer and the organohalide segment or the non-halogenated organic segment without introducing additional linking material may, if desired, be used in accordance with the invention. Most commonly, however, the linker will include two or more reactive moieties, as described above, connected by a spacer element. The presence of such a spacer permits bifunctional linkers to react with specific functional groups within the corticosteroid and the bulky or charged group, resulting in a covalent linkage between the two. The reactive moieties in a linker may be the same (homobifunctional linker) or different (heterobifunctional linker, or, where several dissimilar reactive moieties are present, heteromultifunctional linker), providing a diversity of potential reagents that may bring about covalent attachment between the trifunctional monomer and the non-halogenated organic segment or water insoluble segment.

Spacer elements in the linker typically consist of linear or branched chains and may include a $C_{1-10}$ alkyl, a heteroalkyl of 1 to 10 atoms, a $C_{2-10}$ alkene, a $C_{2-10}$ alkyne, $C_{5-10}$ aryl, a cyclic system of 3 to 10 atoms, or —$(CH_2CH_2O)_n$ $CH_2CH_2$—, in which n is 1 to 4.

Biologically Active Agents

The coatings of the invention include one or more biologically active agents. The incorporation can be achieved by mixing the self assembling coating components (for example, an oligofluorinated oligomer (e.g., a branched or linear oligofluorinated oligomer) or a branched compound including water insoluble segments) and the biologically active agent together and applying the mixture to the surface of the article prior to implantation. In some instances, the biologically active agent is covalently tethered or complexed to an oligomeric compound (for example, an oligofluorinated oligomer (e.g., a branched or linear oligofluorinated oligomer) or a branched compound including water insoluble segments), preferably a branched compound, in the self assembling coating. A detailed description of how biologically active agents may be covalently tethered or complexed to an oligofluorinated oligomer is provided in U.S. Pat. No. 6,770,725 and U.S. Patent Publication No. 20070037891, each of which is incorporated herein by reference. Biologically active agents that can be used in the methods and compositions of the invention include therapeutic, diagnostic, and prophylactic agents. They can be naturally occurring compounds, synthetic organic compounds, or inorganic compounds. Biologically active agents that can be used in the methods and compositions of the invention include, but are not limited to, proteins, peptides, carbohydrates, antibiotics, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogrel and ramatroban, antibodies, neurotransmitters, psychoactive drugs, oligonucleotides, proteins, lipids, and any biologically active agent described herein.

Exemplary therapeutic agents include growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutylric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active agent can be an antiinflammatory agent, such as an NSAID, corticosteriod, or COX-2 inhibitor, e.g., rofecoxib, celecoxib, valdecoxib, or lumiracoxib.

Exemplary diagnostic agents include imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials.

A preferred biologically active agent is a substantially purified peptide or protein. Proteins are generally defined as consisting of 100 amino acid residues or more; peptides are less than 100 amino acid residues. Unless otherwise stated, the term protein, as used herein, refers to both proteins and peptides. The proteins may be produced, for example, by isolation from natural sources, recombinantly, or through peptide synthesis. Examples include growth hormones, such as human growth hormone and bovine growth hormone; enzymes, such as DNase, proteases, urate oxidase, alronidase, alpha galactosidase, and alpha glucosidase; antibodies, such as trastuzumab.

Rapamycin Macrolides

Rapamycin (Sirolimus) is an immunosuppressive lactam macrolide that is produced by *Streptomyces hygroscopicus*. See, for example, McAlpine, J. B., et al., J. Antibiotics 44: 688 (1991); Schreiber, S. L., et al., J. Am. Chem. Soc. 113: 7433 (1991); and U.S. Pat. No. 3,929,992, incorporated herein by reference. Exemplary rapamycin macrolides which can be used in the methods and compositions of the invention include, without limitation, rapamycin, CCI-779, Everolimus (also known as RAD001), and ABT-578. CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Antiproliferative Agents

Exemplary antiproliferative agents which can be used in the methods and compositions of the invention include, without limitation, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™ (Novartis), leflunomide (Pharmacia), SU5416 (Pharmacia), SU6668 (Pharmacia), PTK787 (Novartis), Iressa™ (AstraZeneca), Tarceva™, (Oncogene Science), trastuzumab (Genentech), Erbitux™ (ImClone), PKI166 (Novartis), GW2016 (GlaxoSmithKline), EKB-509 (Wyeth), EKB-569 (Wyeth), MDX-H210 (Medarex), 2C4 (Genentech), MDX-447 (Medarex), ABX-EGF (Abgenix), CI-1033 (Pfizer), Avastin™ (Genentech), IMC-1C11 (ImClone), ZD4190 (AstraZeneca), ZD6474 (AstraZeneca), CEP-701 (Cephalon), CEP-751 (Cephalon), MLN518 (Millenium), PKC412 (Novartis), 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026DHA-paclitaxel, Taxoprexin, TPI-287, Sphingosine-based lipids, and mitotane.

Corticosteroids

Exemplary corticosteroids which can be used in the methods and compositions of the invention include, without limitation, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisol one, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar anti-inflammatory properties are also intended to be encompassed by this group.

NSAIDs

Exemplary non-steroidal antiinflammatory drugs (NSAIDs) which can be used in the methods and compositions of the invention include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

Analgesics

Exemplary analgesics which can be used in the methods and compositions of the invention include, without limitation, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine and dihydroacetorphine.

Antimicrobials

Exemplary antimicrobials which can be used in the methods and compositions of the invention include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Local Anesthetics

Exemplary local anesthetics which can be used in the methods and compositions of the invention include, without limitation, cocaine, procaine, lidocaine, prilocalne, mepivicaine, bupivicaine, articaine, tetracaine, chloroprocaine, etidocaine, and ropavacaine.

Antispasmodics

Exemplary antispasmodics which can be used in the methods and compositions of the invention include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

Coatings

The coatings of the invention can be designed to vary in adhesion to a surface by varying the size of oligomers, their solubility in physiological media, and/or employing oligomers which favorably interact with the surface on which the coating is placed. Such favorable interactions can include, for example, coordinatation (i.e., carboxylate groups coordinating to a metal surface), and/or hydrogen bonding between the oligomers and the device surface. In certain embodiments, the self assembling coating is applied to the surface of the implantable medical device to form a thin coating (i.e., 0.5-50.0 microns in thickness). Because the coatings of the invention do not have the properties of a base polymer, they are not susceptible to flaking or cracking during the physical manipulation of the device, such as the crimping and deployment of a stent. The coatings of the invention can control the release of biologically active agents incorporated within the self assembling coating by limiting the rate of diffusion of the agent from the self assembling coating prior to disruption of the coating (e.g., by deformation of the coating, or by exposing the coating to an energy source).

A primary function of such coating can be to increase efficacy of local delivery of a biologically active agent for a defined period of time. The self assembling coating is optionally complexed, or covalently tethered, or physically combined with a biologically active agent, or applied in a mixture including a biologically active agent. The amount of biologically active agent loaded into the self assembling coating will depend upon the desired local concentration and release profile from the self assembling coating.

In some embodiments, the coatings of the invention contain a water insoluble segment (e.g., fluorinated segment) which provides a desired surface fluorine factor. The fluorinated moiety, functions as a shield to biological agent incorporated within the self assembling coating, from undesirable interaction with physiological media (e.g. fluid and blood components). This allows effective dose transfer of the active agent to the target site with limited transfer of the delivery platform. The biologically active agent can be covalently bound to an oligomeric compound (for example, an oligofluorinated oligomer (e.g., a branched or linear oligofluorinated oligomer) or a branched compound including water insoluble segments), preferably a branched compound, as described herein, in the self assembling coating via a hydrolyzable linker. In these embodiments, it is understood that the hydrolysis of the linker can occur either within the self assembling coating or after diffusion of the biologically active agent from the surface of the device. It is desirable to limit hydrolytic degradation near the site of implantation to avoid localized changes in pH and the generation of inflammatory side products.

The coatings of the invention can be applied to the surface of a medical device in any number of ways including, but not limited, to electrodeposition, dipping, spraying, brushing, printing, or spin coating of the self assembling coating material from a solution or suspension followed by solvent removal step as needed. Further description of how the coatings can be made and applied is found in the Examples.

The self assembling coating can be formed by combining the components, one or more oligomeric compounds (for example, an oligofluorinated oligomer (e.g., a branched or linear oligofluorinated oligomer) or a branched compound including water insoluble segments), preferably branched compounds, and biologically active agents, in solution, as solid or suspension. The self assembling coating can be applied onto the surface of medical device followed by solvent removal step as needed. Alternatively, the components of a coating can be applied in a layered fashion (e.g., an oligofluorinated oligomer (e.g., a branched or linear oligofluorinated oligomer) or a branched compound including water insoluble segments can be applied onto the surface of medical device as a base layer, followed by biologically active agents as the top layer (e.g., the biologically active agent(s) can be in combination with a branched oligomeric compound such as an oligofluorinated oligomer), or an oligofluorinated oligomer (e.g., a branched or linear oligofluorinated oligomer) or a branched compound including water insoluble segments, preferably a branched oligomeric compound, can be applied to medical device surface as a top coat, enveloping the base layer of biologically active agent(s) (e.g., can be in combination with the oligofluorinated oligomer (e.g., a branched or linear oligofluorinated oligomer) or branched compound including water insoluble segments)). Multiple alternating layers can be applied, as needed. Optionally, the self assembling coatings of the invention can include a cofactor binder to improve the binding of the self assembling coating to the device surface or the component composition of the self assembling coating. The coatings can be formed by mixing the oligofluorinated oligomer (e.g., a branched or linear oligofluorinated oligomer) or branched compound including water insoluble segments, cofactor binder, and biologically active agent(s), and applied to the surface of medical device. Such coatings can be formed by applying the oligofluorinated oligomer (e.g., a branched or linear oligofluorinated oligomer) or a branched compound including water insoluble segments as the base coat, followed by biologically active agents as the top coat with cofactor binder layer in the middle, or vice versa. Cofactor binders which can be used in the coatings of the invention include, without limitation, carbowax, gelatin, albumin gel, dextrose, iodine salt, polysaccharide, lipids, nucleic acid, PEG, sodium citrates, dicalcium phosphate, lactose, sucrose, glucose, mannitol, silicic acid, carboxymethylcellulose, alginates, gelatin, polyvinylpyrrolidone, acacia, glycerol, agar-agar, paraffin, pluronic gel, glycerol monostearate, kaolin, calcium/magnesium stearate, solid polyethylene glycols, sodium lauryl sulfate, and propylene glycol.

The self assembling coatings of the invention can also be applied directly to a tissue surface to be treated. When applied directly, the components of the coating can be mixed and applied onto the surface being treated. With this approach it is desirable to employ an excretable oligomeric compound (e.g., oligofluorinated oligomer (e.g., a branched or linear oligofluorinated oligomer) or a branched compound including water insoluble segments), preferably a branched compound, in the self assembling coating.

Coated Medical Devices

A wide variety of implantable medical devices can be coated using the compositions and methods of the invention to improve their biocompatibility and to deliver biologically active agents at a desired site of treatment. The medical devices can include transient medical devices, non-implantable vascular, non-vascular, percutaneous, and cutanous devices. Percutaneous devices include items that penetrate the skin, thereby extending from outside the body into the body. Cutaneous devices are used superficially. Percutaneous devices include categories that penetrates the skin, thereby extending from outside the body into the body, without limitation, catheters of various types, balloon catheter, neuron guiding catheter, neuron microcatheter, neuron microwire, neuron balloon, coronary wires, coronary guiding catheter, stent grafts, stent delivery system, coronary wires, coronary guiding catheter, introducer sheath, dilator, guidewire, syringe needle, dialysis sheath cannulas, filters, drainage tubes such as chest tubes, surgical instruments such as forceps, retractors, needles, and catheter cuffs.

The transient medical devices of the invention can include energy sources including ultrasound, heat, electromagnetic, and/or vibrational energy sources for disrupting the self assembling coating and releasing the biologically active agent. For example, an ultrasound external energy source may be used having a frequency in a range from 20 kHz to 100 MHz, preferably in a range from 0.1 MHz to 20 MHz, and an intensity level in a range from 0.05 W/cm$^2$ to 10 W/cm$^2$, preferably in a range from 0.5 W/cm$^2$ to 5 W/cm$^2$. The ultrasound energy would be directed at the self assembling coating and either continuously applied or pulsed, for a time period in a range from 5 sec to 30 minutes, preferably in a range from 1 minute to 15 minutes. Alternatively, the temperature of the surface of the transient medical device can be heated (e.g., in the range of from 36° C. to 48° C.), vibrated, or subjected to electromagnetic energy to facilitate the release of biologically active agent at the desired place and time.

In another approach, the self assembling coating is disrupted mechanically upon deformation of the surface of the device (e.g., expansion of the device). For example, the transient medical devices of the invention can include a radially expandable segment that can be converted from a small diameter configuration to a radially expanded, usually cylindrical, configuration which is achieved when the expandable structure is positioned at a desired target site. The expandable structure may be minimally resilient, e.g., malleable, thus requiring the application of an internal force to expand and set it at the target site. Typically, the expansive force can be provided by a balloon, or another self-expanding structure. Expandable transient medical devices for use in the present invention can utilize a resilient material, such as a tempered stainless steel, or a superelastic alloy such as a Nitinol™ alloy, and forming the body segment so that it possesses its desired, radially-expanded diameter when it is unconstrained, i.e. released from the radially constraining forces of a sheath. The self-expanding expandable structure can be tracked and delivered in its radially constrained configuration, e.g., by placing the expandable structure within a delivery sheath or tube and removing the sheath at the target site. The dimensions of the expandable structure will depend on its intended site of use. Typically, the expandable structure will have a length in a range from about 5 mm to about 100 mm, usually being from about 8 mm to about 50 mm, for vascular applications. The diameter of a cylindrically shaped expandable structure for vascular applications, in a non-expanded configuration, usually ranges from about 0.5 mm to about 10 mm, more usually from about 0.8 mm to about 8 mm; with the diameter in an expanded configuration ranging from about 1.0 mm to about 100 mm, preferably from about 2.0 mm to about 30 mm. The expandable structure usually will have a thickness in a range from about 0.025 mm to 2.0 mm, preferably from about 0.05 mm to about 0.5 mm.

Drug Eluting Balloon (DEB)

Vascular occlusive diseases are mainly caused by changes in pathophysiobiology of the vasculature, resulting in thickening of the vessel lining from fatty deposits or plaques. The most popular mode of therapy for vascular occlusive diseases is the surgical bypass. However, endovascular interventions have been recognized and practiced as an alternative and viable mode of therapy. Balloon angioplasty is designed to expand occluded blood vessels based on balloon inflation, and compression of plaque, allowing perfusion of the diseased tissue. In most endovascular interventions a guiding catheter is advanced in the patient's vasculature until the distal tip of the guiding catheter is located close to the targeted location. A guidewire is advanced out of the distal end of the guiding catheter into the patient's blood vessel, until the distal end of the guidewire crosses a lesion to be dilated. A dilation catheter having an inflatable balloon on the distal portion thereof is advanced into the patient's blood vessel over previously introduced guidewire until the balloon of the dilatation catheter is properly positioned across the lesion. The success of the endovascular intervention is generally high, but the vessel patency is often reduced due to restenosis in the vicinity of the original lesion causing re-occlusion of the vessel. The ability to locally deliver pharmaceuticals from a balloon surface provides an approach in controlling restenosis. The entire or partial external balloon surface can be coated with a desired pharmaceutical, the time of balloon inflation or the multiplicity of inflation can also be controlled, making the "drug eluting balloon" an adaptable and robust tool for local drug delivery.

The compositions and methods of this invention can be used in various applications of drug eluting balloon technology, such as percutaneous translumenal angioplasty (PTA), coronary angioplasty (PTCA), neurovascular angioplasty (PTNA), balloon aortic valvuplasty (BAV). Furthermore, the composition of the invention allows incorporation of various biological agents depending on the application of the drug eluting balloons.

In one application, DEB can also be used as balloon aortic valvuplasty to repair stenotic aortic valve which has become stiff from calcium buildup. The balloon is inserted and inflated into the aortic valve to increase the opening size of the valve and improving blood flow. Traditional balloon aortic valvuloplasty many times fails to prevent restenosis in patients. Drug eluting balloon in this case allows the incorporated antirestenotic drug to elute into dilated aortic valves to prevent restenosis post-treatment.

In another application, DEB can be used to treat peripheral diseases which are not treatable by stenting. This is particularly true for vessels below the knee in which the vessels are small and the stent struts break under the torque.

One possible non-vascular application of drug eluting balloon is localized chemotherapy. Balloon catheter can be coated with anticancer agent and introduced to cancerous tissue.

Balloons for angioplasty are categorized as high pressure balloons. A standard balloon consists of a cylindrical body, two conical tapers, and two necks. The particular angles and shapes of the balloon can be customized depending on the application and particularities of the physiology. High pressure balloons are also used to dilate constrictions and blockages in other areas such as the esophagus, biliary-duct, urethra, fallopian-tube, heart-valve, tear-duct and carpel-tunnel dilation. Other applications for high pressure balloons include positioning, occlusion, light therapy, heat transfer and endovascular graft delivery.

High pressure balloons are made from noncompliant or low-compliant materials (expand only 5-10%) which have controllable size and shape. Thin-walled, these balloons exhibit high tensile strength with relatively low elongation. Currently most high pressure balloons are made from PET or nylon. PET has high tensile strength with a maximum pressure rating. It can be molded to have ultra thin walls (5-50 mm) with diameters from 0.5-50 mm. Nylon is softer and can be easily refolded for easier withdrawal into the guiding catheter. Both materials have demonstrated compatibility to coatings which provide lubricity, abrasion and puncture resistance, conductivity, thrombogenicity, drug release, and reflectivity, among other characteristics. The rated pressure for angioplasty is 2-20 atm. Larger diameter balloons have a lower rated pressure as the stress in the balloon wall increases when inflated to the nominal diameter. PTCA balloon catheters are usually 2-4 mm in diameter, 10-40 mm in length and have a rate pressure of 10-20 atm. PTA balloon catheters are usually 4-14 mm in diameter and 20-200 mm in length and have a rate pressure of 8-20 atm.

Formulations

The oligofluorinated oligomer (e.g., a branched or linear oligofluorinated oligomer) or a branched compound including water insoluble segments, preferably the branched compound, and the biologically active agent of the invention can be formulated as a homogenous solid or solution, solution dispersion (single or multi phase). The conformational arrangement and compatibility of the biologically active agent and oligofluorinated oligomer (e.g., a branched or linear oligofluorinated oligomer) or branched compound including water insoluble segments will guide the efficacy of formulation based on release profile, and solubility enhancing effect.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

ACRONYMS

The following acronyms denote the listed compounds.
BAL poly(difluoromethylene),α-fluoro-ω-(2-hydroxyethyl)
CDCl$_3$ deuterated chloroform
DBDL dibutyltin dilaurate
DCM dichloromethane
DIC diisopropylcarbodiimide
DMAc dimethylacetamide
DMAP 4-(dimethyamino)pyridine
DMF dimethylformamide
DMSO dimethylsulphoxide
EtO ethylene oxide
HCl hydrochloric acid
KBr potassium bromide
KD dansyl labelled lysine
LDI lysine diisocyanate
MeOH methanol
NaOH sodium hydroxide
N$_2$ nitrogen gas
PBS phosphate buffer solution
PCL polycaprolactone
PTMO polytetramethylene oxide
PTX paclitaxel
SA salicylic acid
TEA triethylamine
THF tetrahydrofuran
TMX m-tetramethylxylene diisocyanate

EXAMPLES

Example 1

Synthesis and Characterization of Compound 1
(Oligofluoro-Ester)

PTMO (15.0 g, 14 mmol) was reacted with LDI (5.9 g, 28 mmol) in DMAc (80 mL) in the presence of DBDL catalyst, at 70° C. for two hours under N$_2$. Perfluoroalcohol (13.15 g, 31 mmol) was dissolved in DMAc (25 mL), added to the reaction, and stirred at room temperature overnight under N$_2$. The product (Compound 1) was purified by solvent extraction and cationic SPE. GPC (dioxane mobile phase): retention time of 25 minutes. $^1$H NMR (400 MHz, CDCl$_3$) δ (ppm) 4.24-4.46 (—CH$_2$—O, BAL), 3.94-4.13 (—CH$_2$—O—CO, PTMO), 3.74 (CH$_3$, LDI), 3.28-3.50 (CH$_2$—O, PTMO), 2.98-3.28 (CH$_2$—NH, LDI), 2.29-2.60 (—CH$_2$—CF$_2$—, BAL), 1.16-1.96 (PTMO and LDI CH$_2$). IR analysis was in accordance with the chemical structure: 3318 cm$^{-1}$ (N—H) H-bonded, 2930 cm$^{-1}$ (C—H), 2848 cm$^{-1}$ (C—H), 1712 cm$^{-1}$ (C=O) urethane amide, 1524 cm$^{-1}$ (C—N), 1438 cm$^{-1}$ (C—N), 1356 cm$^{-1}$ (C—O), 1400-1000 cm$^{-1}$ (C—F). Elemental analysis: 20% F. DSC analysis: T$_g$=−69° C. Compound 1 was further purified by dissolving in MeOH and dialyzing for three days using 1000 MWCO regenerated cellulose membranes.

Example 2

Synthesis and Characterization of Compound 2
(Oligofluoro-Acid)

Compound 1 was dissolved in MeOH and treated with 1N NaOH. The product (Compound 2) was neutralized with 1N HCl, precipitated in water, and dried. GPC (dioxane mobile phase): retention time of 25 minutes. NMR (400 MHz, CDCl$_3$) δ (ppm) 4.26-4.48 (—CH$_2$—O, BAL), 3.96-4.23 (—CH$_2$—O—CO, PTMO), 3.30-3.52 (CH$_2$—O, PTMO), 3.07-3.22 (CH$_2$—NH, LDI), 2.36-2.55 (—CH$_2$—CF$_2$—, BAL), 1.14-1.94 (PTMO and LDI CH$_2$). IR analysis was in accordance with the chemical structure: 3318 cm$^{-1}$ (N—H) H-bonded, 2930 cm$^{-1}$ (C—H), 2848 cm$^{-1}$ (C—H), 1712 cm$^{-1}$ (C=O) urethane amide, 1524 cm$^{-1}$ (C—N), 1438 cm$^{-1}$ (C—N), 1356 cm$^{-1}$ (C—O), 1400-1000 cm$^{-1}$ (C—F). Compound 2 was further purified by dissolving in MeOH and dialyzing for three days using 1000 MWCO regenerated cellulose membranes.

Example 3

Synthesis and Characterization of Compound 3
(Dansyl Oligofluoro)

Compound 2 (2.0 g, 1.71 mmol acid) was dissolved in anhydrous DMF (25 mL). The solution was chilled, DIC (0.215 g, 1.71 mmol) was added and the solution was stirred for 2 hours at room temperature under $N_2$. TEA (0.345 g, 3.41 mmol) and dansyl-labelled lysine (KD) (0.718 g, 1.71 mmol) in anhydrous DMF (9 mL) were added to the activated Compound 2, and the solution was kept well stirred for 12 hours at room temperature under $N_2$. The product (Compound 3) was purified with cationic and fluorous SPE, and recovered by rotary evaporation. GPC (dioxane mobile phase): no free KD was detected, and the polymer peak had strong UV absorbance. $^1$H NMR (400 MHz, $CDCl_3$) δ (ppm) 7.14-8.59 (aromatic H, KD) 4.46-4.66 ($CH_2$—N, KD), 4.28-4.48 (—$CH_2$—O, BAL), 3.90-4.17 (—$CH_2$—O—CO, PTMO), 3.31-3.54 ($CH_2$—O, PTMO), 3.06-3.26 ($CH_2$—NH, LDI), 2.81-3.00 ($CH_3$, KD) 2.32-2.58 (—$CH_2$—$CF_2$—, BAL), 1.08-1.94 ($CH_2$, PTMO, LDI and KD). High performance liquid chromatography (HPLC) analysis of Compound 3: samples ranging in concentration from 0.0005 to 50 mg/mL in MeOH were injected and analyzed using MeOH/pH 9 buffer mobile phase. Free KD (standard solution) eluted at 21 minutes, and Compound 3 eluted at 35 minutes with no evidence of free KD contamination.

Example 4

Synthesis and Characterization of Compound 4 (Silicone Oligofluoro)

Hydroxy terminated PDMS (10 g, 13.8 mmol) was reacted with LDI (5.848 g, 28 mmol) in DMAc (80 mL) in the presence of DBDL catalyst, at 70° C. for two hours under $N_2$. Perfluoroalcohol (12.745 g, 30 mmol) was dissolved in DMAc (32 mL), added to the reaction, and stirred at room temperature overnight under $N_2$. GPC (THF mobile phase): retention time of 25.5 minutes. $^1$H NMR (400 MHz, $CDCl_3$) δ (ppm) 4.26-4.48 (—$CH_2$—O, BAL), 3.93-4.09 (—$CH_2$—O—CO, PDMS), 3.74 ($CH_3$, LDI), 3.08-3.26 ($CH_2$—NH, LDI), 2.33-2.60 (—$CH_2$—$CF_2$—, BAL), 1.61-1.76 (—Si—O—$CH_2$, PDMS), 1.13-1.93 ($CH_2$, LDI), 0.49-0.60 ($CH_2$—$CH_2$—$CH_2$, PDMS), 0.025-0.36 ($CH_3$, PDMS). DSC analysis: $T_g$=−40° C. Elemental Analysis: 21.2% F.

Example 5

Synthesis and Characterization of Compound 5 (BPH Oligofluoro)

Neopentyl glycol phthalic anhydride based polyester diol (BPH, 10.0 g, 10 mmol) was reacted with LDI (4.24 g, 20 mmol) in anhydrous DMAc (70 mL) in the presence of DBDL catalyst, at 70° C. for two hours under $N_2$. Perfluoroalcohol (9.24 g, 22 mmol) was dissolved in anhydrous DMAc (25 mL), added to the reaction, and stirred at room temperature overnight under $N_2$. The product (Compound 5) was purified by solvent extraction and cationic SPE. GPC (THF mobile phase): retention time of 25.4 minutes. $^1$H NMR (400 MHz, $CDCl_3$) δ (ppm) 7.41-7.79 (aromatic H, BPH), 4.25-4.44 (—$CH_2$—O, BAL), 4.05-4.21 (—$CH_2$—O, BPH), 3.67-3.79 (—$CH_3$, LDI), 3.06-3.25 ($CH_2$—NH, LDI), 2.32-2.56 (—$CH_2$—$CF_2$—, BAL), 1.26-1.90 ($CH_2$, LDI), 0.86-1.11 (—$CH_3$, BPH). Surface analysis (XPS): 31.4% F. Elemental analysis: 15.64% F. DSC analysis: $T_g$=25° C. Contact angle (water advancing): 106°. Texture analysis: 1.8 g. Compound 5 was further purified by dissolving in acetone and dialyzing for three days using 1000 MWCO regenerated cellulose membranes.

Example 6

Synthesis and Characterization of Compound 6 (PEG Oligofluoro)

PEG (7.65 g, 7.65 mmol) was reacted with LDI (3.25 g, 15.3 mmol) in anhydrous THF (54 mL) in the presence of DBDL catalyst, at 70° C. for two hours under $N_2$. Perfluoroalcohol (7.07 g, 16.8 mmol) was dissolved in anhydrous THF (18 mL), added to the reaction, and stirred at room temperature overnight under $N_2$. The product (Compound 6) was purified by precipitation and cationic SPE. GPC (THF mobile phase): retention time of 24 minutes. $^1$H NMR (300 MHz, $CDCl_3$) δ (ppm) 4.25-4.44 (—$CH_2$—O, BAL), 4.08-4.15 (—$CH_2$—O—CO, PEG), 3.70-3.75 (—$CH_3$, LDI), 3.55-3.77 (—$CH_2$, PEG), 3.10-3.30 ($CH_2$—NH, LDI), 2.32-2.60 (—$CH_2$—$CF_2$—, BAL), 1.20-1.90 ($CH_2$, LDI). DSC analysis: $T_g$=−45.5° C., $T_m$=21.7° C. Contact angle analysis (water advancing): 108.7°. Compound 6 was further purified by dissolving in acetone and dialyzing for three days using 1000 MWCO regenerated cellulose membranes.

Example 7

Synthesis and Characterization of Compound 7 (NPG542 Oligofluoro)

Neopentyl glycol (NPG, 3.0 g, 28.8 mmol) was reacted with LDI (7.63 g, 36 mmol) in anhydrous THF (133 mL) in the presence of DBDL catalyst, at 70° C. for two hours under $N_2$. Perfluoroalcohol (6.65 g, 15.8 mmol) was dissolved in anhydrous THF (83 mL), added to the reaction, and stirred at room temperature overnight under $N_2$. The product (Compound 7) was purified by precipitation and cationic SPE. GPC (THF mobile phase): retention time of 26 minutes. $^1$H NMR (300 MHz, $CDCl_3$) δ (ppm) 4.23-4.48 (—$CH_2$—O, BAL), 3.85-4.10 (—$CH_2$—O—CO, NPG), 3.70-3.73 (—$CH_3$, LDI), 3.10-3.20 ($CH_2$—NH, LDI), 2.30-2.58 (—$CH_2$—$CF_2$—, BAL), 1.25-1.85 ($CH_2$, LDI), 0.80-1.05 ($CH_3$, NPG). Surface analysis (XPS): 18.75% F. Elemental analysis: 14.46% F. DSC analysis: $T_g$=−3° C., $T_m$=161° C. Contact angle analysis (water advancing): 106.9° C. Texture analysis: 1 g. Compound 7 was further purified by dissolving in acetone and dialyzing for three days using 1000 MWCO regenerated cellulose membranes.

Example 8

Synthesis and Characterization of Compound 8 (PEGA Oligofluoro)

Poly(diethylene adipate) (PEGA, 7.45 g, 2.98 mmol) was reacted with LDI (1.26 g, 5.96 mmol) in anhydrous DMAc (43.5 mL) in the presence of DBDL catalyst, at 70° C. for two hours under $N_2$. Perfluoroalcohol (2.75 g, 6.55 mmol) was dissolved in anhydrous DMAc (7 mL), added to the reaction, and stirred at room temperature overnight under $N_2$. The product (Compound 8) was purified by precipitation and cationic SPE. GPC (THF mobile phase): retention time of 22.5 minutes. NMR (300 MHz, $CDCl_3$) δ (ppm) 4.30-4.40 (—$CH_2$—O, BAL), 4.20-4.30 (—$CH_2$—O—CO, PTMO; —NH—OCO—O—$CH_2$—$CH_2$—, PEGA), 3.75 ($CH_3$, LDI), 3.58-3.72 (—O—$CH_2$—$CH_2$—O—, PEGA), 3.12-3.24 ($CH_2$—NH, LDI), 2.30-2.70 (—$CH_2$—$CF_2$—, BAL; —COO—O—$CH_2$—, PEGA), 1.25-2.0 ($CH_2$ LDI; —$CH_2CH_2CH_2$—, PEGA). Surface analysis (XPS): 41.06% F. Elemental analysis: 25.76% F. Contact angle analysis (water advancing): 118.5°. DSC analysis: $T_g$=−43° and 156°. Viscosity analysis (37° C.): 144 Pa·s. Texture analysis: 66 g. Compound 8 was further purified by dissolving in acetone and dialyzing for three days using 1000 MWCO regenerated cellulose membranes.

Example 9

Synthesis and Characterization of Compound 9 (HPCN TMX Oligofluoro)

Hexamethylene polycarbonate diol (HPCN, 25.0 g, 12.5 mmol) was reacted with LDI (6.10 g, 25 mmol) in anhydrous DMAc (150 mL) in the presence of DBDL catalyst, at 70° C. for two hours under $N_2$. Perfluoroalcohol (11.55 g, 27.5 mmol) was dissolved in anhydrous DMAc (29 mL), added to the reaction, and stirred at room temperature overnight under $N_2$. The product (Compound 9) was purified by solvent extraction and cationic SPE. GPC (dioxane mobile phase): retention time of 22.6 minutes. $^1$H NMR (300 MHz, CDCl$_3$) δ (ppm) 7.2-7.45 (—CH, TMX), 4.30-4.43 (—CH$_2$—O, BAL), 4.04-4.20 (—CH$_2$—CH$_2$—O—CO, HPCN), 3.90-4.03 (—CH$_2$—O—CO—NH, HPCN), 2.25-2.55 (—CH$_2$—CF$_2$—, BAL), 1.13-1.80 (CH$_2$, HPCN; CH$_3$, TMX). Elemental analysis: 10.5% F. DSC analysis: $T_g$=−32.2° C., $T_m$=147° C. Surface analysis (XPS): 33.17% F. Viscosity analysis (37° C.): 360 Pa·s. Texture analysis: 170 g. Compound 9 was further purified by dissolving in acetone and dialyzing for three days using 1000 MWCO regenerated cellulose membranes.

Example 10

Synthesis and Characterization of Compound 10 (EG Oligofluoro)

Ethylene glycol (EG, 1.5 g, 24.2 mmol) was reacted with LDI (10.3 g, 48.4 mmol) in anhydrous THF (60 mL) in the presence of DBDL catalyst, at 70° C. for two hours under $N_2$. Perfluoroalcohol (22.4 g, 53.2 mmol) was dissolved in anhydrous THF (56 mL), added to the reaction, and stirred at room temperature overnight under $N_2$. The product (Compound 10) was purified by precipitation and cationic SPE. GPC (THF mobile phase): retention time of 27 minutes. $^1$H NMR (300 MHz, CDCl$_3$) δ (ppm) 4.23-4.48 (—CH$_2$—O, BAL), 4.10-4.25 (—CH$_2$—O—CO, EG), 3.75 (—CH$_3$, LDI), 3.10-3.28 (CH$_2$—NH, LDI), 2.36-2.60 (—CH$_2$—CF$_2$—, BAL), 1.25-1.85 (CH$_2$, LDI). Surface analysis (XPS): 36.87% F. Elemental analysis: 27.51% F. DSC analysis: $T_g$=−3° C. Contact angle analysis (water advancing): 130.7°. Viscosity analysis) (37°: 2397 Pa·s. Texture analysis: 29.1 g.

Example 11

Synthesis and Characterization of Compound 11 (HPH Oligofluoro)

1,6-hexanediol-phthalic anhydride based polyester diol (HPH, 20.0 g, 10 mmol) was reacted with LDI (4.24 g, 20 mmol) in anhydrous THF (122 mL) in the presence of DBDL catalyst, at 70° C. for two hours under $N_2$. Perfluoroalcohol (9.24 g, 22 mmol) was dissolved in anhydrous THF (23 mL), added to the reaction, and stirred at room temperature overnight under $N_2$. The product (Compound 11) was purified by precipitation and cationic SPE. GPC (THF mobile phase): retention time of 23.8 minutes. $^1$H NMR (300 MHz, CDCl$_3$) δ (ppm) 7.52-7.68 (—CH, aromatic ring HPH), 4.30-4.40 (—CH$_2$—O, BAL), 4.10-4.22 (—CH$_2$—O—CO, HPH), 4.0-4.08 (—CH$_2$—COO—NH—, HPH), 3.70-3.75 (—CH$_3$, LDI), 3.10-3.21 (CH$_2$—NH, LDI), 2.32-2.52 (—CH$_2$—CF$_2$—, HAL), 1.24-1.85 (CH$_2$, LDI and HPH). DSC analysis: $T_g$=−13° C. Contact angle analysis (water advancing): 119.1°. Surface analysis (XPS): 40.74% F. Elemental analysis: 9.18% F. Viscosity analysis (37° C.): 896 Pa·s. Texture analysis: 113.9 g. Compound 11 was further purified by dissolving in acetone and dialyzing for three days using 1000 MWCO regenerated cellulose membranes.

Example 12

Synthesis and Characterization of Compound 12 (P3611 Oligomer)

Polyalkoxylated polyol (P3611) (1 g, 3.8 mmol) was reacted with LDI (2.391 g, 11.28 mmol) in DMAc (17 mL) in the presence of DBDL catalyst, at 70° C. for two hours under $N_2$. Perfluoroalcohol (5.211 g, 12.4 mmol) was dissolved in DMAc (13 mL), added to the reaction, and stirred at room temperature overnight under $N_2$. GPC (THF mobile phase): retention time of 23 minutes. $^1$H NMR (300 MHz, CDCl$_3$) δ (ppm) 4.25-4.51 (—CH$_2$—O, BAL), 3.93-4.07 (—CH$_2$—O—CO, P3611), 3.73 (C$_{1-3}$, LDI), 3.05-3.25 (CH$_2$—NH. LDI), 2.31-2.57 (—CH$_2$—CF$_2$—, BAL), 1.21-1.93 (CH$_3$—CH$_2$—, P3611, and CH$_2$, LDI), 0.79-0.95 (CH$_3$, P3611). Elemental Analysis: 33% F.

Example 13

Synthesis and Characterization of Compound 13 (Hexafluoro Pentanediol Oligofluoro)

2,2,3,3,4,4-Hexafluoro-1,5-pentanediol (HPD, 1.04 g, 4.9 mmol) was reacted with LDI (2.07 g, 9.75 mmol) in anhydrous DMAc (20 mL) in the presence of DBDL catalyst at 70° C. for two hours under $N_2$. Methanol (417 μL) was added to the reaction, and stirred at room temperature overnight under $N_2$. Solvent was removed and the product (Compound 12) was purified by cationic SPE. GPC analysis: the product was dissolved in dioxane and run on a GPC system with a polystyrene column and UV detector. $^1$H NMR (400 MHz, CDCl$_3$) δ (ppm) 4.53-4.75 (—CH$_2$—CF$_2$, HPD), 4.30-4.40 (—CH, LDI), 3.70 (—CH$_3$, LDI), 3.60-3.65 (CH$_3$—O, MeOH), 3.10-3.25 (CH$_2$—NH, LDI), 1.25-1.85 (C$_{1-12}$, LDI). Compound 12 was blended into a Carbothane 85A base polymer as a 5 wt % additive, using DMAc solvent to make a 0.1 g/mL solution. Films of the blend were cast in Teflon molds, and dried at 50° C. for 24 hours, followed by drying under vacuum at 50° C. for 24 hours. Surface analysis of film blend (XPS): 1.78% F.

Example 14

Synthesis and Characterization of Compound 14 (Perfluoro Dodecanediol Oligofluoro)

1H,1H,12H,12H-Perfluoro-1,12-dodecanediol (PDD, 1.02 g, 1.81 mmol) was reacted with LDI (0.77 g, 3.63 mmol) in anhydrous DMAc (20 mL) in the presence of DBDL catalyst at 70° C. for two hours under $N_2$. Methanol (158 μL) was added to the reaction, and stirred at room temperature overnight under $N_2$. Solvent was removed and the product (Compound 14) was purified by cationic SPE. GPC analysis: the product was dissolved in dioxane and run on a GPC system with a polystyrene column and UV detector. $^1$H NMR (400

MHz, CDCl$_3$) δ (ppm) 4.53-4.75 (—CH$_2$—CF$_2$, PDD), 4.30-4.40 (—CH, LDI), 3.70 (—CH$_3$, LDI), 3.60-3.65 (CH$_3$—O, MeOH), 3.10-3.25 (CH$_2$—NH, LDI), 1.25-1.85 (CH$_2$, LDI). Compound 14 was blended into a Carbothane 85A base polymer as a 5 wt % additive, using DMAc solvent to make a 0.1 g/mL solution. Films of the blend were cast in Teflon molds, and dried at 50° C. for 24 hours, followed by drying under vacuum at 50° C. for 24 hours. Surface analysis of film blend (XPS): 35.63% F.

Example 15

Synthesis and Characterization of Compound 15 (Bis-hydroxyphenyl hexafluoropropane)

2,2-Bis(4-hydroxyphenyl) hexafluoropropane (BHP, 1.08 g, 3.21 mmol) was reacted with LDI (1.37, 6.44 mmol) in anhydrous DMAc (20 mL) in the presence of DBDL catalyst at 70° C. for four hours under N$_2$. Methanol (290 µL) was added to the reaction, and stirred at room temperature overnight under N$_2$. The product (Compound 15) was isolated by removing solvent. GPC analysis: the product was dissolved in dioxane and run on a GPC system with a polystyrene column and UV detector. $^1$H NMR (400 MHz, DMSO) δ (ppm) 6.98-7.03 (—CH—CCF$_3$, BHP), 6.75-6.83 (—CH—CO, BHP), 4.53-4.75 (NH, LDI), 4.30-4.40 (—CH, LDI), 3.65 (—CH$_3$, LDI), 3.45-3.51 (CH$_3$—O, MeOH), 3.10-3.25 (CH$_2$—NH, LDI), 1.25-1.85 (CH$_2$, LDI). Compound 15 was blended into a Carbothane 85A base polymer as a 5 wt % additive, using DMAc solvent to make a 0.1 g/mL solution. Films of the blend were cast in Teflon molds, and dried at 50° C. for 24 hours, followed by drying under vacuum at 50° C. for 24 hours. Surface analysis of film blend (XPS): 3.82% F.

Example 16

Synthesis and Characterization of Compound 16 (HEMA Conjugated Oligofluoro)

Compound 2 (10.0 gram, ~8 mmol acid), DMAP (0.488 gram, 4 mmol), HEMA (6.247 gram, 48 mmol), and DCM (50 mL) were added to a 250 mL flask, and stirred until all compounds were dissolved. EDC (4.600 gram, 24 mmol) was added to the DCM solution, and once the EDC was dissolved, the solution was stirred at room temperature for 24 hours under N$_2$ and protected from light. The reaction mixture was reduced to a viscous liquid by rotary evaporation (25° C.) and washed three times with water (3×400 mL). The washed product was dissolved in diethyl ether (100 mL, 100 ppm BHT), and water was removed by mixing the solution with MgSO$_4$ for 1 hour. The solution was clarified by gravity filtration into a 250 mL flask, and the solvent was removed by rotary evaporation (25° C.). The product (Compound 16) was re-dissolved in DMF and was purified using fluorous SPE (F—SPE) and recovered by rotary evaporation. NMR (300 MHz, CDCl$_3$) δ (ppm) 6.09-6.15 (HEMA vinyl H), 5.58-5.63 (vinyl H, HEMA), 4.83-5.78 (—CH$_2$), 4.27-4.49 (CH$_2$—O, BAL; CH$_2$, HEMA), 4.01-4.15 (CH$_2$—OCO—, PTMO), 3.75 (small CH$_3$ signal), 3.31-3.50 (CH$_2$—O—, PTMO), 3.07-3.23 (CH$_2$—NH, PTMO), 2.36-2.56 (CH$_2$—CF$_2$—, BAL), 1.91-1.96 (CH$_3$, HEMA) 1.27-1.74 (CH$_2$, PTMO and LDI). GPC analysis (dioxane mobile phase): retention time of 26.5 minutes. No free HEMA monomer detected in this analysis. IR analysis: 1634 cm$^{-1}$ (C=C).

Example 17

Synthesis and Characterization of Compound 17 (FEO1 Oligofluoro)

PTMO (10 g, 0.0097 mol, degassed) was dissolved in anhydrous DMAc (50 mL). Lysine diisocyanate (4.11 g, 0.020 mol, distilled) and DBDL catalyst was dissolved in anhydrous DMAc (25 mL) and was added dropwise to the PTMO solution. The pre-polymer reaction was maintained at 60-70° C. for two hours under a nitrogen atmosphere. The perfluoroacrylate (4,4,5,5,6,6,7,7,8,8,9,9,10,10,11,11 heptadecafluoro-2-hydroxyundecyl acrylate) (FEO1, 12.058 g, 0.022 mol) was dissolved in DMAc (25 mL) with DBDL and added dropwise to the pre-polymer solution, stirred overnight under N$_2$ at room temperature. The product was precipitated in water (2 L), re-dissolved in diethyl ether (100 mL, 100 ppm BHT), dried with MgSO$_4$ and filtered. The ether solution was dropped into hexane (400 mL) to precipitate the product and extract un-reacted reagent. The hexane was decanted and the solvent extraction procedure was repeated twice. The purified product (Compound 17) was dissolved in diethyl ether (50 mL), and the solvent removed by rotary evaporation at room temperature. $^1$H NMR (400 MHz, CDCl$_3$) δ (ppm) 6.40-6.52 (vinyl H, FEO1), 6.09-6.23 (vinyl H, FEO1), 5.80-5.95 (vinyl H, FEO1), 4.15-4.53 (C—H, FEO1; O—CH$_2$—FEO1), 4.00-4.15 (—CH$_2$—O—CO, PTMO), 3.75 (CH$_3$, LDI), 3.31-3.50 (CH$_2$—O, PTMO), 3.05-3.25 (CH$_2$—NH, LDI), 2.35-2.61 (—CH$_2$—CF$_2$—, FEO1), 1.25-1.73 (CH$_2$, PTMO and LDI). GPC analysis (dioxane mobile phase): retention time of 26 minutes. No free FEO1 monomer detected in this analysis. IR analysis: 1634 cm$^{-1}$ (C=C).

Example 18

Synthesis and Characterization of Compound 18 (FEO3 Oligofluoro)

PTMO (10 g, 0.0097 mol, degassed) was dissolved in anhydrous DMAc (50 mL). Lysine diisocyanate (4.241 g, 0.02 mol, distilled) and dibutyltin dilaurate catalyst was dissolved in anhydrous DMAc (22 mL) and was added dropwise to the PTMO solution. The pre-polymer reaction was maintained at 60-70° C. for two hours under N$_2$. The perfluoroacrylate (3-(perfluoro-3-methylbutyl)-2-hydroxypropyl methacrylate) (FEO3, 9.068 g, 0.022 mol) was dissolved in DMAc (23 mL) with dibutyltin dilaurate and added dropwise to the pre-polymer solution. The reactor was stirred overnight at room temperature under N$_2$. The product was precipitated in water (2 L), re-dissolved in diethyl ether (100 mL, 100 ppm BHT), dried with MgSO$_4$ and filtered. The ether solution was dropped into hexane (400 mL) to precipitate the product and extract un-reacted reagent. The hexane was decanted and the solvent extraction procedure was repeated two times. The purified product (Compound 18) was dissolved in diethyl ether (50 mL), and the solvent removed by evaporation in a flow hood at room temperature. $^1$H NMR (400 MHz, CDCl$_3$) δ (ppm) 6.10-6.16 (vinyl H, FEO3), 5.66-5.89 (vinyl H, FEO3), 4.27-4.41 (—O—CH$_2$—, FEO3), 4.15-4.27 (—O—CH$_2$—, FEO3) 4.00-4.14 (—CH$_2$—O—CO, PTMO), 3.75 (CH$_3$, LDI), 3.27-3.52 (CH$_2$—O, PTMO), 3.05-3.21 (CH$_2$—NH, LDI), 2.34-2.61 (—CH$_2$—CF$_2$—, FEO3), 1.90-1.99 (CH$_3$, FEO3), 1.22-1.90 (CH$_2$, LDI and PTMO). GPC analysis (dioxane mobile phase): retention time of 26.5 minutes. No free FEO3 monomer detected in this analysis. IR analysis: 1634 cm$^{-1}$ (C=C).

Example 19

Synthesis and Characterization of Compound 19 (Tris Oligofluoro)

Method A: EDC Conjugation of Tris

Compound 2 (10 g, 4.4 mmol), EDC, and DMAP (in a 1:6:0.5 molar ratio of acid groups: EDC:DMAP) were dissolved in anhydrous DMF (200 mL). Tris (in a 1.1:1 molar ratio of Tris:acid groups) was added to the reaction mixture. This solution was reacted under $N_2$ for 24 hours at room temperature. The DMF solvent was evaporated at 40° C. The viscous residual was extracted with diethyl ether (3×100 mL) at room temperature. EDC and Tris are insoluble in cold ether. The clear ether solution was evaporated. The white viscous product (Compound 19-a) was dried under vacuum at 40° C. overnight. Elemental analysis: 25.57% F. IR analysis: 3330 cm$^{-1}$ (O—H), 1110 cm$^{-1}$ (C-OH,) 1160 cm$^{-1}$ (C—F), 1220 cm$^{-1}$ (C—O—C). $^1$H NMR (300 MHz, CDCl$_3$) δ (ppm) 2.38 (C$_{Tris}$CH$_2$OH), 1.73 (C$_{Tris}$—NH). Determination of the OH number: the hydroxyl content of Compound 19-a (which is unique to the pendent Tris) was determined by reacting Compound 19-a with excess acetic anhydride in pyridine, followed by back-titration with potassium hydroxide base using phenolphthalein as an indicator. Result: OH number 2.4113 mmol/g.

Method B: K$_2$CO$_3$ Conjugation of Tris

Compound 1 (3.05 g, ~2.6 mmol) was dissolved in anhydrous methanol (100 mL). A mixture of tris hydroxymethyl aminoethane (Tris, 0.63 g, 5.2 mmol) and anhydrous potassium carbonate (0.72 g, 5.2 mmol) was added. This reaction mixture was refluxed at 45° C. for seven days. The reaction mixture was cooled, and the solution was purified using cationic exchange and fluorous solid phase reaction. The final product (Compound 19-b) was dried under vacuum for 48 hours (50° C.). NMR (300 MHz, CDCl$_3$) δ (ppm) 4.25-4.50 (—CH$_2$—O, BAL), 3.95-4.20 (—CH$_2$—OCO—, PTMO), 3.75 (reduced CH$_3$ signal, LDI), 3.57-3.83 (CH$_2$, Tris), 3.30-3.56 (—CH$_2$O, PTMO), 3.04-3.28 (—CH$_2$NH—, PTMO), 2.29-2.59 (CH$_2$CF$_2$—, BAL), 1.17-1.97 (—CH$_2$—, PTMO and LDI). HPLC analysis (Reversed phase HPLC, C18 column, methanol and pH 9 PBS mobile phase (gradient)): elution time of 34.6 minutes. Compound 19-b was blended into a Carbothane 85A base polymer as a 5 wt % additive, using DMAc solvent to make a 0.1 g/mL solution. Films of the blend were cast in Teflon molds, and cured at 50° C. for 24 hours, followed by drying under vacuum at 50° C. for 24 hours. The air-contacting surface of the film was analyzed by XPS, using a 90° take-off angle. Elemental analysis: Carbothane 0% F; Carbothane+5 wt % Compound 19-b 36.3% F. Contact angle analysis: Compound 19-b was blended into Carbothane 85A and ethylene-co-vinyl acetate (EVA) base polymer as 5 wt % mixtures, using solvent casting techniques. Contact angle analysis was performed using water EVA. 105°±/−2° (hydrophobic), EVA+Compound 19-b: 15°±/−2° (hydrophilic). Carbothane 85A: 102°±/−4° (hydrophobic), Carbothane+Compound 19-b: 18°±/−5° (hydrophilic).

Example 20

Synthesis and Characterization of Compound 20 (Tris-Br Oligofluoro)

Compound 19 (Tris oligofluoro) (10 g, 4.0 mmol) (dried previously) and TEA (in a 1.2:1 molar ratio of TEA:OH groups) were dissolved in anhydrous CH$_2$Cl$_2$ (50 mL) under $N_2$. The solution was cooled in an ice-water bath. A stoichiometric quantity of 10% BIBB/CH$_2$Cl$_2$ solution was added dropwise to Compound 19/CH$_2$Cl$_2$ solution under a nitrogen atmosphere. The mixture was stirred for 24 hours at room temperature and was then filtered to remove the TEA-HBr salt. The filtrate was washed with water (10 mL) three times. The CH$_2$Cl$_2$ was evaporated at room temperature. A pale brown viscous solid product (Compound 20) was obtained. Elemental analysis: 17.42% F, 13.65% Br. $^1$H NMR (300 MHz, CDCl$_3$) δ (ppm) 2.05 (C(CH$_3$)$_2$Br).

Example 21

Synthesis and Characterization of Compound 21 (Tris-PHEMA-Br Oligofluoro)

Compound 20 (Tris-Br oligofluoro) (2.5 g, 1 mmol) was dissolved in DMF (10 mL). CuBr (0.143 g, 1 mmol) and HMTETA (0.253 g, 1.1 mmol) were added into the solution. The flask was connected to a vacuum line and was freeze-thawed three times by liquid nitrogen. The flask was filled with ultrahigh-purity nitrogen and freshly distilled HEMA (2.86 g, 22 mmol) was added. The flask was heated in an oil bath to 50° C. for 20 hours. The polymerization was stopped by cooling the flask in ice water. DMF was evaporated from the solution at 40° C. The viscous solid was dissolved in THF and filtered through a silica gel column to remove the catalyst. After evaporating THF from the filtrate at room temperature, the solid product (Compound 21) was dried under vacuum at 40° C. overnight. Elemental analysis: 10.21% F; 0.28% Br. $^1$H NMR (300 MHz, DMSO) δ (ppm) 4.80 (CH$_2$OH, HEMA), 3.92 (COOCH$_2$, HEMA), 3.60 (CH$_2$OH, HEMA), 1.79 (CH$_2$CCH$_3$, HEMA), 0.80 (CH$_2$CCH$_3$, HEMA). The average (polystyrene equivalent) molecular weight was recorded as 9.01×10$^4$ g/mol with polydispersity of 1.65. The weight average MW of the final product was substantially larger than Compound 20. This data indicated a successful polymerization of the final product. Based on OH titration, the average degree of polymerization can be determined for the PHEMA portion of the molecule. The theoretical OH number was 6.366 mmol/g, and the titrated value was 6.386 mmol/g. Based on the OH number, the HEMA was quantitatively incorporated and the average degree of polymerization for the PHEMA branch was 21.7.

Example 22

Synthesis and Characterization of Compound 22 (Tris-PMAA-Br Oligofluoro)

Tert-butyl methacrylate (tBMA, 2.10 g, 15 mmol), CuBr (0.149 g, 1 mmol), and xylene (4 mL) were added to a flask. The flask was sealed with a rubber septum and cooled in ice water. Ultrahigh-purity nitrogen was purged through the mixture for 15 minutes. Then, HMTETA (previously purged with nitrogen; 0.46 g, 2.0 mmol) was added by syringe. After the solution became clear and light green in color, a solution of Compound 20 (0.5858 g, 1 mmol of Br group) in acetone (5 mL) was added. The flask was heated in an oil bath to 70° C. overnight. The polymerization was stopped by cooling the flask in ice water. The solution was diluted with THF (20 mL) and filtered through a silicon gel column to remove the catalyst. The filtrate was precipitated in water, and the solid polymer was dried under vacuum at 30° C. overnight. The solid polymer (1 g) was dissolved into a solution of CHCl$_3$ (9 mL) and CF$_3$COOH (1 mL). The solution was stirred at room temperature for 20 hours. The polymer became a gel-like semi solid in the solution. The solvent was removed by filtration, and the solid was washed with $CHCl_3$ twice and filtered. All liquid residuals were removed under vacuum at room temperature. The solid product (Compound 22) was dried under vacuum at 40° C. overnight. The number of COOH titrated was 8.8592 mmol/g. Based on titration results and the stoichiometry, the tBMA conversion was determined to be 96.7%, and the average degree of polymerization of the PMAA branch calculated was 14.6.

Example 23

Synthesis and Characterization of Compound 23 (Tris-PVP-Br Oligofluoro)

1-Vinyl-2-pyrrolidone (VP, 3.33 g, 30 mmol), Compound 20 (1 mmol), and CuBr (0.143 g, 1 mmol) were added to a flask. The flask was sealed with a rubber septum and cooled in ice water. The mixture was purged with $N_2$ for 30 minutes. 2,2'-Dipyridyl (BPY, previously purged with $N_2$, 0.156 g, 1 mmol) was added to the mixture. The flask was heated in an oil bath to 100° C. for 20 hours. The polymerization was stopped by cooling the flask in ice water. The solution was diluted with $CH_2Cl_2$ (200 mL) and filtered through an alumina column to remove the catalyst. After evaporating the $CH_2Cl_2$ from the filtrate at room temperature, the solid product was dried under vacuum at 40° C. overnight. Elemental analysis: 0.67% F; 1.10% Br. Based on F and Br content, the VP conversion reached 78.6%, translating to an average degree of polymerization for the PVP branch of 60. $^1$H NMR (300 MHz, $CDCl_3$) δ (ppm) 7.00 ($CH_2C\underline{H}$, PVP), 4.92 (C$\underline{H}_2CH$, PVP), 3.48 (NC$\underline{H}_2$, PVP), 3.40 (C$\underline{H}_2$O$C\underline{H}_2$, polyurethane), 2.47 ($COCH_2$, PVP), 2.10 ($CH_2C\underline{H}_2CH_2$, PVP), 1.62 ($CH_2C\underline{H}_2C\underline{H}_2CH_2$, polyurethane).

Example 24

Synthesis and Characterization of Compound 24 (Accmer Oligofluoro)

Accmer (7.0 g, 7.0 mmol) was reacted with LDI (2.97 g, 14 mmol) in anhydrous DMAc (50 mL) in the presence of DBDL catalyst at 70° C. for 2 hours under $N_2$. Perfluoroalcohol (6.45 g, 15.4 mmol) was dissolved in anhydrous DMAc (16.2 mL), added to the reaction, and stirred at room temperature overnight under $N_2$. The product (Compound 24) was purified by cationic SPE. GPC (THF mobile phase): retention time of 25.5 minutes. $^1$H NMR (300 MHz, $CDCl_3$) δ (ppm) 4.24-4.46 (—$CH_2$—O, BAL), 3.94-4.13 (—$CH_2$—O—CO, Accmer), 3.75 ($CH_3$, LDI), 3.38-3.64 ($CH_2$—O, Accmer), 3.16 (C$\underline{H}_2$—NH, LDI), 2.29-2.60 (—$CH_2$—$CF_2$—, BAL), 1.16-1.96 ($CH_2$, Accmer and LDI), 0.84 ($CH_3$, Accmer). DSC analysis: $T_g$=−47° C., $T_m$=23° C. Elemental analysis: 17% F. Compound 24 was further purified by dissolving in acetone and dialyzing for three days using 1000 MWCO regenerated cellulose membranes. Elemental analysis: 13.3% F. Compound 24 was drop casted onto nylon for surface analysis (XPS): 45% C, 29% F, 5% N, 21% O.

Example 25

Synthesis and Characterization of Compound 25 (Accmer TMX Oligofluoro)

Accmer (3.0 g, 3.0 mmol) was reacted with TMX (1.466 g, 6.0 mmol) in anhydrous DMAc (25 mL) in the presence of DBDL catalyst at 70° C. for 2 hours under $N_2$. Perfluoroalcohol (2.778 g, 6.0 mmol) was dissolved in anhydrous DMAc (25 mL), added to the reaction, and stirred at room temperature overnight under $N_2$. The product had a GPC (THF mobile phase) retention time of 27 minutes. The product was purified by cationic SPE. $^1$HNMR analysis was in accordance with the expected chemical structure. $^1$HNMR (300 MHz, $CDCl_3$) δ (ppm) 7.1-7.6 (aromatic-$CH_2$, TMX), 4.3-4.4 (—$CH_2$—O, BAL; —NH-urethane), 3.9-4.0 (—$CH_2$—O—CO, Accmer), 3.4-3.8 (—$CH_2$—O—, Accmer), 3.38 (—$CH_2$—, Accmer), 2.3-2.5 (—$CH_2$—$CF_2$—, BAL), 1.5-2.0 (—$CH_3$, TMX), 1.2 (—$CH_3$, Accmer), 0.9 (—$CH_3$, Accmer). Elemental analysis: 17% F. Compound 25 was drop casted onto nylon for surface analysis (XPS): 54% C, 27% F, 3% N, 15% O.

Example 26

Synthesis and Characterization of Compound 26 (Accmer HDI Oligofluoro)

Accmer (3.0 g, 3.0 mmol) was reacted with HDI (1.009 g, 6.0 mmol) in anhydrous DMAc (25 mL) in the presence of DBDL catalyst at 70° C. for 2 hours under $N_2$. Perfluoroalcohol (2.778 g, 6.0 mmol) was dissolved in anhydrous DMAc (25 mL), added to the reaction, and stirred at room temperature overnight under $N_2$. The product had a GPC (THF mobile phase) retention time of 25 minutes. The product was purified by cationic SPE. $^1$HNMR analysis was in accordance with the expected chemical structure. $^1$HNMR (300 MHz, $CDCl_3$) δ (ppm) 4.3-4.4 (—$CH_2$—O, BAL; —NH-urethane), 3.9-4.0 (—$CH_2$—O—CO, Accmer), 3.5-3.7 (—$CH_2$—O—, Accmer; N$\underline{H}$—COO—, HDI-Accmer urethane), 3.38 (—$CH_2$—, Accmer), 3.1-3.25 (NH—$C\underline{H}_2$—, HDI), 2.3-2.5 (—$CH_2$—$CF_2$—, BAL), 1.3-1.6 (—$CH_2$—, HDI), 0.9 (—$CH_3$, Accmer). Compound 26 was drop casted onto nylon for surface analysis (XPS): 44% C, 46% F, 3% N, 7% O.

Example 27

Synthesis and Characterization of Compound 27 (Accmer THDI Oligofluoro)

Accmer (3.0 g, 3.0 mmol) was reacted with THDI (1.045 g, 6.0 mmol) in anhydrous DMAc (25 mL) in the presence of DBDL catalyst at 70° C. for 2 hours under $N_2$. Perfluoroalcohol (2.778 g, 6.0 mmol) was dissolved in anhydrous DMAc (25 mL), added to the reaction, and stirred at room temperature overnight under $N_2$. The product had a GPC (THF mobile phase) retention time of 25 minutes. The product was purified by cationic SPE. $^1$HNMR analysis was in accordance with the expected chemical structure. $^1$HNMR (300 MHz, $CDCl_3$) δ (ppm) 4.3-4.4 (—$CH_2$—O, BAL; —NH-urethane), 3.9-4.0 (—$CH_2$—O—CO, Accmer), 3.4-3.8 (—$CH_2$—O—, Accmer), 3.38 (—$CH_2$—, Accmer), 2.3-2.5 (—$CH_2$—$CF_2$—, BAL), 1.2 (—$CH_3$, Accmer), 0.9 (—$C_{1-13}$, Accmer). Elemental analysis: 12% F. Compound 27 was drop casted onto nylon for surface analysis (XPS): 55% C, 25% F, 3% N, 17% O.

Example 28

Sterilization of Selected Compounds and Balloon Catheter

Selected compounds from Examples 1-27 were weighed into polypropylene conical tubes capped with lint-free tissue, placed in sterilization pouches, and were sterilized by EtO. The sterilized compounds were analyzed by GPC, and these results were compared to the pre-sterilization profile. No changes were observed for pre and post sterilization samples.

Compound 24 and PTX complex was prepared according to the established protocol, weighed into polypropylene conical tube capped with lint-free tissue, placed in sterilization pouches, and sterilized by EtO. The sterilized complex was analyzed by GPC and HPLC and compared to its profile pre sterilization. No changes observed were observed in both Compound 24 and PTX post sterilization.

Balloon catheters coated with Compound 1, Compound 24, and Compound 24+PTX were also sterilized by EtO. Sterilized and non-sterilized balloon catheters were analyzed by GPC, and pre- and post sterilization molecular weight profile compared. MW pre-sterilization: Compound 1: 8655, Compound 24: 4212, Compound 24+PTX: 4212. MW post sterilization: Compound 1: 8960, Compound 24: 4841, Compound 24+PTX: 4849. PTX HPLC retention time (min): Pre-sterilization: 12.202, post sterilization: 12.192.

Example 29

Assessment of Biodistribution and Clearance in In-Vivo Model

Compound 3 (15 mg) was dissolved in DMSO (25 µL, 0.6 g/mL) and injected in male Sprague-Dawley rats. Whole blood samples were taken regularly over a 24 hr period. Compound 3 fluorescent signal in the whole blood samples were measured by microplate analysis (excitation: 320 nm and emission: 540 nm). Urine samples were also analyzed for Compound 3 fluorescent signal. $K_e=0.044$ $hr^{-1}$, $T_{1/2(e)}$, $T_{1/2(Total)}=15.7$ hr.

Example 30

Visualizing Coating Coverage on Balloon Catheter

PTCA balloon catheters as received, slightly deployed and unwrapped were dip coated and sprayed in a solution of Compound 3 in 90:10 toluene:THF and dried in a 50° C. flow over overnight. The balloon catheter was slightly deployed using a glass syringe and 18 G tubing. Sprayed balloons were coated with an EFD spray system with settings specific to Compound 3. Coating was evaluated with a short wave UV lamp. The unwrapped balloon catheter had the most continuous coating, followed by the slightly inflated and the wrapped balloon.

Example 31

Coating Compound 1 on a Balloon Catheter and Evaluation of Coating Pre and Post Deployment in Air Compound 1 (1.0 g) was dissolved in THF, and kept at room temperature until use. The solution was sprayed onto slightly deployed PTCA balloon catheters using an EFD spray system with settings specific to Compound 1, and dried in a 50° C. flow oven overnight. SEM analysis suggested a thin, even coating pre and post deployment in air.

Example 32

Preparation of Compound 1+PTX, and PTX Loading of a Coated Balloon Catheter

Compound 1 (0.4 g) and PTX (0.04 g-1.6 g) were dissolved in THF, and used immediately. Balloon catheters (3.0 mm×17 mm) were either sprayed or dip-coated. Sprayed balloons were coated with an EFD spray system with settings developed specifically for Compound 1. For dip coating, balloon catheters were secured in place with small clamps while the dipping solution was raised to a specified height using a scissor lift table. Coated balloons were stripped in appropriate solvent overnight. PTX loading was measured using RP-HPLC with benzonitrile as the internal standard. Loading was controlled by changing number of dips or sprays ($ug/mm^2$): 0.2-6.0.

Example 33

Evaluation of Inflammatory Cell Response to Compounds 1, 2, 5-11, 16-18, 24

Compounds 1, 2, 5-11, 24 were dissolved in THF or toluene, and were cast into 96 well polypropylene plates. The solvent was evaporated at room temperature for 24 hours, then placed in a 60° C. flow oven for 24 hours, and finally dried under vacuum overnight. Compounds 16-18 were dissolved in toluene containing BPO initiator (1 wt % of Compounds 16-18 mass). The toluene solution was cast into 96 well polypropylene plates and placed in a semi-enclosed chamber at room temperature for 1 day. Compounds 16-18 films were then cured for 12 hours in an $N_2$ purged 60° C. oven, and vacuum dried. For comparison purposes, films of SIBS and 316 stainless steel inserts were added to the plates. The plates were sterilized under a UV lamp for 1 hour, after which each sample well was hydrated with PBS. U937 monocyte-like cells (2.5×105 cells) were seeded into each well in the presence of PMA, and the plates were incubated at 37° C. in a humid incubator for three days. Non-adherent cells were removed, and adherent U937 macrophages were enumerated using a CyQuant assay.

Example 34

Migration of HCAEC Through Membranes Coated with Selected Compounds and 10 wt % PTX Compound 1 (0.1 g) was dissolved in MeOH (0.5, 1, 2 and 4 mL), and these solutions (0.05 mL) were pipetted onto and wicked through a BD 8 µm PET membrane insert. Compound 1 was also blended with PTX to form 1 and 10 wt % solutions, and these were coated onto membranes. As a control, a solution of SIBS polymer of suitable concentration was coated onto membranes. The resulting coated membranes were examined by SEM and porosity was confirmed by the passage of water through the membranes. Further, Compound 3 was coated using the same method, and fluorescence (Ex 320, Em 540 nm) was measured to confirm the presence of coating: (uncoated membrane)=3.5, (Compound 1)=0.6, (Compound 3)=28.2. HCAEC were cultured to third passage using media and supplements supplied by Lonza, and were starved in serum-free media overnight. Cells were lifted and re-suspended in 0.5% FBS media, and HCAEC were seeded (80 000 per membrane insert). The lower wells were filled with 20% FBS media. The negative control consisted of an uncoated membrane with 0.5% FBS media in the lower well. The positive control consisted of an uncoated membrane with 20% FBS media in the lower well. After four hours of incubation, the wells were lifted out, the inner membranes were scrubbed free of cells, and the lower membrane surface was fixed and stained with DiffQuik. Images of the membranes were collected by microscopy, and cell morphology characteristics and population were recorded.

The migration assay as described for the HCAEC was repeated with cell lines from other species on all Compounds described in Examples 1, 5, 7-11.

Example 35

Evaluation of Platelet and Fibrinogen Interaction with Films of Compounds 1, 16 and 17

Compound 1 was dissolved in toluene and stirred for 24 hours at room temperature. The solution was sprayed onto 4 cm×4 cm 316L stainless steel coupons using an EFD spray system with settings specific to Compound 1. The coupons were dried in a 50° C. flow oven for 20-24 hours. Compounds 16 and 17 were dissolved in toluene containing BPO initiator (1 wt % of Compounds 16 and 17 mass) and the solution was cast into 4 cm×4 cm PTFE wells (6 mL per well), and the PTFE casting plate was placed in a semi-enclosed chamber at room temperature for 1 day. The Compound 16 and 17 films were then cured for 12 hours in a $N_2$ purged 60° C. oven. Human whole blood was obtained from healthy drug-free volunteers and collected in centrifuge tubes with either acid citrate dextrose anti-coagulant (6 parts ACD to 1 part blood) or low molecular weight heparin to a final concentration of 0.2 U/mL. Platelets from blood collected with ACD were isolated by centrifugation and tagged with 0.5 mCi/mL Na51Cr. Red blood cells were also isolated from the ACD whole blood and washed. The Na51Cr tagged platelets and washed red blood cells were combined with platelet poor plasma to give a final platelet concentration of 250,000 platelets/μL and a 40% hematocrit. Finally, 125I-fibrinogen was added to the whole blood suspension such that it represented approximately 2% of the total amount of fibrinogen. Platelet adhesion was measured from flowing whole blood in a cone-and-plate device which produces laminar flow and a uniform rate of shear. Coated coupons and films were placed in the wells of the cone-and-plate device with 1.2 mL of the whole blood suspension containing Na51Cr platelets and the assay was conducted for 15 minutes. The coupons and films were then rinsed with fresh buffer and the radioactivity was measured with a γ counter and correlated to the number of adherent platelets (Na51Cr platelets) and adsorbed fibrinogen (125I-fibrinogen) based on the radioactivity of the original whole blood suspension. Compared to the uncoated stainless steel coupon, Compounds 1, 16 and 17 significantly reduced platelet adhesion and fibrinogen adsorption.

Example 36

Evaluation of Protein Adhesion with Films of Compound 1

Films of Compound 1 used in Example 35 were also processed to evaluate protein adhesion. Surfaces were rinsed with isotonic tris buffer and then exposed to 2% sodium dodecyl sulfate for 24 hours to elute proteins. SDS-PAGE gels were then performed. Protein bands were not visible suggesting minimal protein adhesion.

Example 37

MEM Elution Assay—Cytotoxicity Assessment of Compounds 1, 2, 5-11, 17 and 18

Compounds 1, 2, and 5-11 were weighed and incubated in MEM media at a 4 g:20 mL ratio for 24 hours at 37° C. Films of Compounds 17 and 18 were treated in the same fashion. L-929 mouse fibroblast cells were seeded and incubated at 37° C. in 5% CO2 to obtain sub-confluent monolayers of cells. The growth medium in triplicate cultures was replaced with MEM extract (2 mL). Triplicate cultures were also prepared as positive and negative controls. Cell cultures were examined under microscope after 24 hours to evaluate cellular characteristics and percent lysis. Under the conditions of this test, the MEM extracts showed no evidence of causing cell lysis or toxicity.

Example 38

Direct contact assay of Compound 1

The viability of HeLa epithelial cells in direct contact with test materials was used to assess the potential cytotoxicity of Compound 1. Samples of Compound 1 were solvent cast on agar-supported Supor filters. Subsequently, a monolayer of HeLa cells were cultured directly on the filter, in the presence of MEM culture media. After 24 hours of incubation, the Supor filter was rinsed and stained with succinic dehydrogenase. Viable cells were identified by a positive purple stain and cytotoxicity was determined by examining the stained filter for cell exclusion zones around the cast material, or a low cell density. Each cytotoxicity assay included a positive and negative control.

Example 39

Dose Dependant Cytotoxicity of Compounds 24 and 18

Compounds 24 and 18 were dissolved in DMSO and added to MEM media at various concentrations. L-929 mouse fibroblast cells were seeded and incubated at 37° C. in 5% CO, to obtain sub-confluent monolayers of cells. The growth medium in triplicate cultures was replaced with Compounds 24 and 18 containing MEM media. Triplicate cultures were also prepared as positive and negative controls. Cell viability was examined after 24 hour incubation by WST-1 assay at 1 mg/ml and reported as % viable compared to control. Compound 24=99.8% and Compound 18=96%.

Example 40

Compound 1, 5, 8, 9, 11, and 24 Compatibility with Various Therapeutic Agents

Compounds 1, 5, 8, 9, and 11 were mixed with Troglitazone, C6-Ceramide, Cerivastatin, Prostaglandin E1, VEGF, Paclitaxel, Rapamycine and Dexamethasone in appropriate solvent at various concentrations. Compound 24 was also mixed with Paclitaxel, C6-Ceramide, Rapamycin, and Ibuprofen. Solutions were drop-casted onto stainless steel coupons or nylon films and visually inspected macroscopically and microscopically for phase separation and crystallization. Compounds 1, 5, 8, 9, 11, and 24 were compatible with a variety of therapeutic agents.

Example 41

PTX Transfer to Cardiac Muscle from Coated Nylon Films

Compounds 2, 6, and 24 (500 mg)+PTX (214 mg) dissolved in THF were drop-casted onto nylon 12 films and dried overnight in a 50° C. flow oven. Thin pieces of porcine cardiac muscle were soaked in porcine whole blood. The coated nylon 12 films were then placed on top of the cardiac muscle for up to 5 minutes. Transferred PTX was quantified by extraction of cardiac muscle in THF and supernatant analyzed by RP-HPLC with benzonitrile as the internal standard. PTX transferred at 30 s, 1 min, and 5 min, respectively: Compound 2: 38.53 ng, 209.09 ng, 508.94 ng; Compound 6: 133.23 ng, 262.39 ng, 1041.07 ng; Compound 24: 1574.86 ng, 3398.16 ng, 11890.32 ng.

Example 42

Ex Vivo Model of PTX Dosage Upon Balloon Deployment

Porcine hearts sourced from local commercial farm suppliers, were harvested and perfused with saline. The drug eluting balloon catheter was advanced into position, and the system was deployed. The location was marked, the balloon was withdrawn, and the segment was fully dissected from the myocardium. Analysis of drug content involved tissue homogenization, solid phase extraction (Waters HLB SPE) of the pharmaceutical, and HPLC analysis. The pharmaceutical remaining on the balloon was solvent extracted and analyzed by HPLC.

Example 43

Retention of PTX on Balloon after Exposure to Blood

Balloon catheters were coated with Compound 24+PTX and dried at room temperature for 4 days. Coated balloon catheters were then exposed to anti-coagulated porcine blood for 5 minutes. The remaining coating on the balloon catheter was extracted with acetonitrile and PTX quantified by RP-HPLC with benzonitrile as the internal standard. % PTX retained on balloon: 72.8%.

Example 44

PTX Release During Deployment in Blood

Balloon catheters were coated with Compound 24+PTX and dried at room temperature for 4 days. Coated balloon catheters were then exposed to anti-coagulated porcine blood for 4 minutes and then inflated and held for 1 minute. The remaining coating on the balloon catheter was extracted with Acetonitrile and PTX quantified by RP-HPLC with benzonitrile as the internal standard. % PTX released: 67.4%.

Example 45

Animal Study in Rabbit Model

Coated and non-coated balloons were included in the study. Briefly, a carotid arteriotomy was performed. The right common carotid artery was isolated, a 5F introducer was placed and advanced, and a control aortoiliofemoral angiogram was performed via a 4F angiographic catheter positioned above aortic bifurcation. Heparin and lidocaine was injected intra-arterially. Coated balloon and non-coated balloons were introduced under fluoroscopic guidance and inflated according to study protocols. Based on the study design the treated vessel was explanted for quantitative analysis of the drug uptake. Methods for drug extraction and quantification were developed and established.

Example 46

Animal Study in Porcine Model

Coated balloon catheters with Compound 24 were inflated in porcine coronary arteries (castrated male farm porcines, Sus scrofa domestica) or placed at the site of inflation, wrapped, for up to 1 minute. Each animal was given ASA (0.081 g) and Clopidogrel (0.075 g) by mouth daily for three days prior to treatment, and was fasted overnight before the procedure. For surgical procedures, after sedation a marginal ear vein was cannulated for infusion of intravenous fluids and medications. The animal was intubated for administration of anesthetic gases and placed on the catheterization table. Under sterile conditions, a vascular introducer sheath was placed in the right carotid artery by surgical cut down. Continuous hemodynamic monitoring and electrocardiographic monitoring was maintained throughout the procedure. Using the guide catheter as a calibration reference, the diameter of the vessel at reference sites proximal and distal to the intended site of implant, as well as the target site diameter, was measured. The remaining coating on the balloon catheter after the procedure was extracted with Acetonitrile and PTX quantified by RP-HPLC with benzonitrile as the internal standard. % PTX released: Wrapped: 60.2; Inflated: 98.8.

Example 47

Assessment of Systemic Levels of Inflammatory Markers (CRP, MCP-1 and IL-6)

Blood was collected by venipuncture phlebotomy, in EDTA and dry tubes according to study protocols. The blood, in EDTA tubes was centrifuged at 3000 rpm for 15 minutes and the plasma was collected and stored at −20° C. Blood collected in dry tubes was left to clot at room temperature for 15 minutes and centrifuged at 3000 rpm for 10 minutes. Serum was then divided and stored. Quantification of CRP was performed on the serum samples using immunological agglutination. MCP-1 and IL-6 were measured from plasma by ELISA colorimetric assay. Standard curves for MCP-1 and IL-6 were prepared with optical density measured at 450 nm wavelength. Results of mean CRP, MCP-1, and IL-6 were statistically compared at each time point using Student's t-tests.

Example 48

Assessment of Therapeutic Retention of Balloon Coating Under Flow Condition (Blood Loop Model)

Anti-coagulated whole porcine blood at 37° C. was pumped by a peristaltic pump through silicone tubing connections. The pump flow rate was set similar to the rate of blood through the coronary arteries (71.4 mL/min). A coated balloon catheter with compound 1 or 24 was placed in the middle of the blood flow for 1 minute. PTX remaining on the balloon catheter was measured by stripping the coating and quantified using RP-HPLC with benzonitrile as the internal standard. % PTX remaining: Compound 1: 94.4%, Compound 24: 52.2%.

Example 49

Assessment of Anti-Fouling Properties of Balloon Coating

Figure 3:
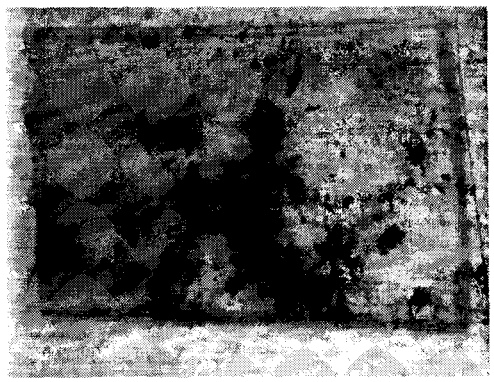
FIG. 3 is a photo representation of BSA-incubated Nylon films coated with Compound 1 showing less protein adsorption (dark blue deposition) than BSA-incubated Nylon films alone. BSA was stained with Coomassie Brilliant Blue R dye.
Figure 3:
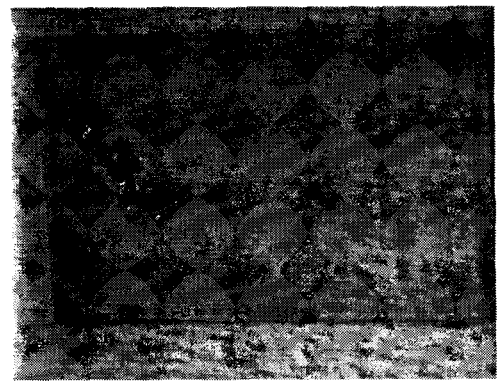

Compound 1 (125 mg) was dissolved in THF (1 mL) and drop casted onto a Nylon film. The Nylon film and Nylon film coated with Compound 1 were qualitatively evaluated for protein adsorption using Coomassie Brilliant Blue R dye, (CBB) after incubating in 1 mL of 500 mg/mL BSA for 40 minutes. Negative controls (without BSA incubation) were also evaluated. After rinsing with distilled water to remove non-adherent protein, 1 mL of 0.25% CBB reagent was added to all samples and incubated for 40 minutes. All samples were rinsed with distilled water and dried. It was shown that BSA-incubated Nylon films coated with Compound 1 showed less protein adsorption (dark blue deposition) than BSA-incubated Nylon films alone (FIG. 3).

Example 50

Assessment of Drug Shielding Effect and Adhesion on Nylon 12 Film Sheet

Compounds 1, 7, and 14 (200 mg/mL) were dissolved in THF. PTX was added to each solution to make a 25 mg/mL solution. Nylon 12 film sheets were cut 1×1 cm size, blend solution was drop cast on the film sheet, dried in a 50° C. flow oven for 1 day. PTX alone was prepared the same way and used as the control. PBS pH 7.4 was pre-warmed to 37° C. Test articles and control articles were incubated in media (4 mL) at 37° C. for 10, 30, 60 and 120 minutes. At the end of each time point, media was exchanged and at the end of the study, the films were stripped with organic solvent, centrifuged, the supernatant collected, and solvent dried overnight at 60° C. The assessment of the drug shielding effect was analyzed by RP-HPLC with benzonitrile as the internal standard. 10 minute PTX release in PBS (ng/mL): Compound 1: 107.6, Compound 7: 79.7, Compound 14: 15.4, PTX alone: 651. The assessment of oligofluoro adhesion on film surface was done by NMR. A calibration curve for each compound was generated by NMR. Stripped coating was re-suspended in $CDCl_3$ (1 mL) and NMR was performed. Quantity of remaining material was back calculated from NMR integration area. Percent remaining material after 120 minute incubation in PBS: Compound 1: 82.1, Compound 7: 85.5. Similar assessment of drug shielding on films was done with porcine whole blood. 10 minute PTX release in blood (%): Compound 1: 28.8, Compound 7: 34.0, Compound 14: 57.4, PTX alone: 75.6.

Example 51

Assessment of Therapeutic Retention of Balloon Coating in a Rabbit Model

Angioplasty was performed normally as in Example 42 with coated balloon catheters. Upon reaching the treatment site, balloon catheter was retracted without deployment. The coating integrity was examined using SEM at the end of study. PTX concentration remained in the coating was measured by stripping the coating and quantified using the following analytical methods: high pressure liquid chromatography (HPLC) and gel permeation chromatography (GPC).

Example 52

Oligofluoro as Solubilizing Agent

Several water insoluble drugs, paclitaxel (PTX), rapamycin, and ibuprofen were complexed with Compound 24 at 4 wt %. Coating was made on nylon film by drop casting method. Control films with drug coated only was also prepared in a same manner. Coated nylon films were incubated in water for 24 hours to measure drug release. Percentage drug released in water: Compound 24+PTX=94, PTX control=11; Compound 24+rapamycin=79, rapamycin control=4; Compound 24+ibuprofen=80, ibuprofen control=40.

Balloon catheters were coated with Compound 24+PTX and non-fluorinated diol+PTX. Balloon catheters were stripped in water to evaluate coating solubility in aqueous solution. PTX measurement from stripped coating in water is the following: Compound 24+PTX=680 µg; non-fluorinated diol+PTX=26 µg.

Example 53

Coating Characterization on Surface of Balloon Catheter

Balloon catheters were coated according to the established protocol (Compound 24+PTX). Coating characterization was done by XPS for wrapped coated balloon, deployed coated balloon, and wrapped uncoated balloon as a control. Surface characterization was done at 4 different points along a single line for each balloon. Percentage of surface fluorine on uncoated balloon: 0.44, 0.26, 0.36, 0.52; on coated balloon (wrapped): 31.39, 30.62, 30.71, 33.78; on coated balloon (deployed): 36.61, 32.71, 32.93, 31.21. Surface characterization suggests a continuous coating throughout the surface of the balloon.

Example 54

High PTX Loading on Balloon Coating

Compound 1 and 24 and non-fluorinated diol were mixed with PTX. Balloon catheters were coated with these solutions and dried according to established method. Coatings were stripped with organic solvent and PTX was measured by HPLC. PTX measurements in Compound 1, Compound 24, and non-fluorinated diol were 961 µg, 713 µg, 466 µg, respectively.

Example 55

Particle Size Analysis

Balloon catheters were coated with Compound 24 and dried at room temperature for 4 days. Coated balloon catheters were exposed to PBS for 1 minute and then inflated and held for 1 minute. Uncoated balloon catheters were used as control. PBS solutions were analyzed for particles using a HIAC Royco Particle Counter with USP33-NF28, Supplement 1, <789><788> as a general guideline. All samples passed the USP <788> limits for SVI (≤100 mL). % Total Differential Particle Counts (5 µm, 10 µm, 25 µm): Control: 79.8, 14.36, 0.11; Compound 24: 81.2, 13.1, 0.32.

Example 56

Acute Systemic Toxicity

A single-dose systemic injection of Compound 24 in PBS (12 mg/mL) was given to 5 Albino Swiss mice and toxicity observed over a 72 hour period. Mice were dosed at 50 mL/kg at an injection rate of ~0.1 mL/sec. Observations for mortality and signs of pharmacological and/or toxicological effects were made immediately post-injection and at 4, 24, 48 and 72 hours post-injection. No clinical signs of toxicity were observed during the study period.

Example 57

Double Coating

Nylon12 films were first treated with a selection of Compounds, and then coated with Compounds containing PTX. PTX release in Tween Buffer for 60 minutes (% Release): Compound 1 alone: 0.7%, Compound 11 and Compound 1: 76%.

Example 58

Assessment of Drug Shielding Effect and Adhesion on Balloon Catheters

Balloon catheters were coated with either Compound 1 (12.5 mg Compound 1, 50 mg PTX, 1 mL THF) or a urea formulation (16 mg urea, 52 mg PTX, 936 µL THF, 104 µL water). Balloon catheters were incubated in PBS for 5 minutes. % PTX release: Compound 1: 0.35, urea: 58.02.

Example 59

Temperature Dependence on Drug Release (PTX Release at Room Temperature and 37° C.)

Compounds 1, 6, 10 were mixed with PTX at 50 wt % in appropriate solvents. PTX containing solution was drop casted on nylon films and dried. Films were incubated in 4 mL PBS at room temperature (RT) and at 37° C. for 1 minute. Coated control films were prepared and stripped in 4 mL organic solvent. PTX release was measured by HPLC. PTX release at RT and 37° C. for Compound 1, 6, and 10:4 ng and 417 ng, 39 ng and 543 ng, 59 ng and 188 ng, respectively.

Example 60

Solvent Free System of Compound 24+PTX

Several compounds were combined with PTX in the previous examples using various solvents. Compound 24 was also combined with PTX using these methods as well as combined in a solvent free system. Compound 24 (75 mg) was warmed in a 60° C. flow oven, added to PTX (3 mg) and mixed. No phase separation was seen macroscopically or microscopically after 24 hours at room temperature.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A transient medical device having a surface with a self assembling coating deposited thereon, said self assembling coating comprising (i) an oligofluorinated oligomer of formula (XV-C):

(XV-C)

$$F_T-L-O-\underset{F_T-L-O}{\overset{}{\underset{}{\bigg\rvert}}}X_1\cdots O\underset{n}{\underbrace{\bigg[\overset{}{\underset{}{\bigg]}}O\bigg]}}\cdots O-X_2$$

wherein
$F_T$ is a polyfluoroorgano group;
L is a linker;
$X_1$ is H, $CH_3$, or $CH_2CH_3$;
$X_2$ is H, $CH_3$, or $CH_2CH_3$; and
n is an integer from 5 to 50;
or
formula (XVII):

(XVII)

$$F_T-O-\overset{O}{\underset{}{\big\Vert}}-NH-L_2-\overset{H}{N}-\overset{O}{\underset{}{\big\Vert}}-O-X_1 \cdots$$

wherein
$F_T$ is a polyfluoroorgano group;
$L_2$ is a substituted or unsubstituted $C_{1-10}$ alkyl, a heteroalkyl of 1 to 10 atoms, a $C_{2-10}$ alkene, a $C_{2-10}$ alkyne, a $C_{5-10}$ aryl, a cyclic system of 3 to 10 atoms, —$(CH_2CH_2O)_qCH_2CH_2$— in which q is an integer of 1 to 10;
$X_1$ is H, $CH_3$, or $CH_2CH_3$;
$X_2$ is H, $CH_3$, or $CH_2CH_3$; and
n is an integer from 5 to 50;
and (ii) a biologically active agent, wherein
said transient medical device comprises an energy generating element, said energy generating element being capable of disrupting said self assembling coating when activated;
or
said transient medical device is a deformable transient medical device which, upon being deployed into a deformed configuration, mechanically disrupts said self assembling coating.

2. A method for delivering a biologically active agent to a site in a vessel, said method comprising inserting into said vessel a transient medical device of claim 1, positioning said transient medical device near said site, and disrupting the coating on said transient medical device deliver said biologically active agent to said site.

3. A method for inhibiting restenosis at a site in a vessel, said method comprising inserting into said vessel a transient medical device of claim 1, and activating said energy generating element, wherein said biologically active agent is selected from antiproliferative agents and rapamycin macrolides.

4. A method for inhibiting restenosis at a site in a vessel, said method comprising inserting into said vessel a deformable transient medical device of claim 1, and deploying said deformable transient medical device into a deformed configuration, wherein said biologically active agent is selected from antiproliferative agents and rapamycin macrolides.

5. The method of claim 2, comprising a bioactive agent and an oligofluorinated oligomer wherein the oligofluorinated oligomer comprises a structure according to formula (XV-C):

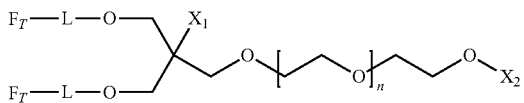

(XV-C)

Wherein
$F_T$ is s a polyfluoroorgano group;
L is a linker;
$X_1$ is H, $CH_3$, or $CH_2CH_3$;
$X_2$ is H, $CH_3$, or $CH_2CH_3$; and
n is an integer from 5 to 50;
or
wherein the oligofluorinated oligomer comprises a structure according to formula (XVII):

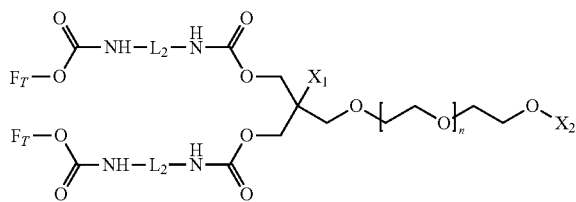

(XVII)

wherein
$F_T$ is a polyfluoroorgano group;
$L_2$ is a substituted or unsubstituted C1-10 alkyl, a heteroalkyl of 1 to 10 atoms, a $C_{2-10}$ alkene, a $C_{2-10}$ alkyne, a $C_{5-10}$ aryl, a cyclic system of 3 to 10 atoms, —$(CH_2CH_2O)_qCH_2CH_2$— in which q is an integer of 1 to 10;
$X_1$ is H, $CH_3$, or $CH_2CH_3$,
$X_2$ is H, $CH_3$, or $CH_2CH_3$; and
n is an integer from 5 to 50.

6. The method of claim 5, wherein said linker is described by formula (XVI):

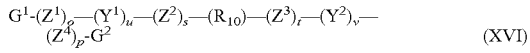

(XVI)

wherein
$G^1$ is a bond between said polyfluoroorgano group and said linker;
$G^2$ is a bond between said linker and an oxygen atom;
$Z^1$, $Z^2$, $Z^3$, and $Z^4$ each, independently, is selected from O, S, and $NR_{11}$;
$R_{11}$ is hydrogen or a $C_{1-10}$ alkyl group;
$Y^1$ and $Y^2$ are each, independently, selected from carbonyl, thiocarbonyl, sulphonyl, or phosphoryl;
o, p, s, t, u, and v are each, independently, 0 or 1; and
$R_{10}$ is a substituted or unsubstituted $C_{1-10}$ alkyl, a heteroalkyl of 1 to 10 atoms, a $C_{2-10}$ alkene, a $C_{2-10}$ alkyne, a $C_{5-10}$ aryl, a cyclic system of 3 to 10 atoms, —$(CH_2CH_2O)_qCH_2CH_2$— in which q is an integer of 1 to 10, or a chemical bond linking $G^1$-$(Z^1)_o$—$(Y^1)_u$—$(Z^2)_s$— to —$(Z^3)_t$—$(Y^2)_v$—$(Z^4)_p$-$G^2$.

7. The method of claim 5, wherein said polyfluoroorgano group is a polyfluoroalkyl having a molecular weight of between 100-1,500 Da;
or
said polyfluoroorgano group is a radical of the general formula $CF_3(CF_2)_rCH_2CH_2$— or $CF_3(CF_2)_s(CH_2CH_2O)_\chi$—, wherein r is an integer from 2 to 20, $\chi$ is an integer from 1 to 10, and s is an integer from 1 to 20
or
said polyfluoroorgano group is a radical of the general formula $CH_mF_{(3-m)}(CF_2)_rCH_2CH_2$— or $CH_mF_{(3-m)}(CF_2)_s(CH_2CH_2O)_\chi$—, wherein m is 0, 1, 2, or 3; $\chi$ is an integer between 1 and 10; r is an integer between 2 and 20; and s is an integer between 1 and 20;
or
said polyfluoroorgano group is selected from $(CF_3)(CF_2)_5CH_2CH_2O$—, $(CF_3)(CF_2)_7CH_2CH_2O$—, $(CF_3)(CF_2)_5CH_2CH_2O$—, $CHF_2(CF_2)_3CH_2O$—, and $(CF_3)(CF_2)_2CH_2O$—, 1H,1H,2H,2H-perfluoro-1-decanol; 1H,1H,2H,2H-perfluoro-1-octanol; 1H,1H,5H-perfluoro-1-pentanol; and 1H,1H, perfluoro-1-butanol, and mixtures thereof.

8. The method of claim 5, wherein said biologically active agent is a hydrophobic drug.

9. The method of claim 8, wherein said hydrophobic drug is selected from antiproliferative agents and rapamycin macrolides.

10. The method of claim 9, wherein said hydrophobic drug is an antiproliferative agent selected from methotrexate, trimetrexate, gemcitabine, vinblastine, vincristine, etoposide, teniposide, topotecan, irinotecan, camptothecin, 9-aminocamptothecin, docetaxel, daunorubicin, doxorubicin, dactinomycin, idarubincin, bleomycin, and tamoxifen, rapamycin, CCI-779, Everolimus, ABT-578, and paclitaxel.

* * * * *